(12) United States Patent
Zhong

(10) Patent No.: US 12,060,606 B2
(45) Date of Patent: *Aug. 13, 2024

(54) BIOSENSORS FOR BIOLOGICAL OR CHEMICAL ANALYSIS AND METHODS OF MANUFACTURING THE SAME

(71) Applicant: MGI Tech Co., Ltd., Shenzhen (CN)

(72) Inventor: Cheng Frank Zhong, Menlo Park, CA (US)

(73) Assignee: MGI Tech Co., Ltd., Shenzhen (CN)

( * ) Notice: Subject to any disclaimer, the term of this patent is extended or adjusted under 35 U.S.C. 154(b) by 496 days.

This patent is subject to a terminal disclaimer.

(21) Appl. No.: 15/803,077

(22) Filed: Nov. 3, 2017

(65) Prior Publication Data

US 2018/0155782 A1 Jun. 7, 2018

Related U.S. Application Data

(60) Provisional application No. 62/416,813, filed on Nov. 3, 2016.

(51) Int. Cl.
| | |
|---|---|
| *H01L 27/146* | (2006.01) |
| *C12Q 1/6874* | (2018.01) |
| *G01N 21/64* | (2006.01) |
| *G01N 21/76* | (2006.01) |

(52) U.S. Cl.
CPC ......... *C12Q 1/6874* (2013.01); *G01N 21/645* (2013.01); *G01N 21/76* (2013.01); *H01L 27/14621* (2013.01); *H01L 27/14627* (2013.01); *H01L 27/14636* (2013.01); *H01L 27/1464* (2013.01); *H01L 27/14645* (2013.01); *H01L 27/14685* (2013.01); *G01N 2021/6471* (2013.01)

(58) Field of Classification Search
CPC ............................... C12Q 1/68; H01L 27/146
See application file for complete search history.

(56) References Cited

U.S. PATENT DOCUMENTS

| | | | |
|---|---|---|---|
| 6,210,891 B1 | 4/2001 | Nyren et al. | |
| 6,325,977 B1 | 12/2001 | Theil | |
| 6,828,100 B1 | 12/2004 | Ronaghi | |
| 6,833,246 B2 | 12/2004 | Balasubramanian | |
| 6,911,345 B2 | 6/2005 | Quake et al. | |
| 7,883,869 B2 | 2/2011 | Ju et al. | |
| 7,910,354 B2 | 3/2011 | Drmanac et al. | |
| 7,972,820 B2 | 7/2011 | Mayer | |
| 8,105,771 B2 | 1/2012 | Drmanac | |
| 8,133,719 B2 | 3/2012 | Drmanac et al. | |
| 8,216,827 B2 | 7/2012 | Pouteau et al. | |
| 8,445,194 B2 | 5/2013 | Drmanac et al. | |
| 8,592,150 B2 | 11/2013 | Drmanac et al. | |
| 8,637,242 B2 | 1/2014 | Shen et al. | |
| 8,778,849 B2 | 7/2014 | Bowen et al. | |
| 8,906,320 B1 | 12/2014 | Eltoukhy et al. | |
| 9,222,132 B2 | 12/2015 | Drmanac | |
| 9,671,344 B2 | 6/2017 | Staker | |
| 10,784,103 B2 | 9/2020 | Li et al. | |
| 11,255,793 B2 | 2/2022 | Zhong et al. | |
| 11,387,096 B2 | 7/2022 | Li et al. | |
| 2006/0084069 A1 | 4/2006 | Chan et al. | |
| 2006/0216856 A1 | 9/2006 | Zhao | |
| 2006/0273430 A1 | 12/2006 | Hua et al. | |
| 2008/0029864 A1 | 2/2008 | Pyo et al. | |
| 2008/0081769 A1 | 4/2008 | Hassibi | |
| 2009/0111207 A1* | 4/2009 | Choumane | G01N 21/6454 438/70 |
| 2010/0204064 A1* | 8/2010 | Cho | G01N 21/6454 506/17 |
| 2010/0277722 A1 | 11/2010 | Kraiczek et al. | |
| 2011/0045466 A1 | 2/2011 | Lin et al. | |
| 2011/0096157 A1* | 4/2011 | Fine | G02B 21/0008 348/79 |
| 2011/0127619 A1 | 6/2011 | Chen et al. | |
| 2011/0172129 A1 | 7/2011 | Lee et al. | |
| 2012/0156100 A1 | 6/2012 | Tsai et al. | |

(Continued)

FOREIGN PATENT DOCUMENTS

| | | |
|---|---|---|
| CN | 102713720 A | 10/2012 |
| CN | 102745638 A | 10/2012 |

(Continued)

OTHER PUBLICATIONS

Toyohasi University, Biosensor Based On A Microelectromechanical System Integrated With a Photodector, Toyohashi University of Technology PhysOrg, 2014, 1-2, obtained from https://phys.org/news/2014-03-biosensor-based-microelectromechanical-photodetector.html on Jan. 14, 2020. (Year: 2014).*
Calabria, D., Dissertation Thesis, Implementation of Chemiluminescence and Color-Based Detection in Smartphone For Bioassays, University of Bologna, Apr. 2016, 1-128. (Year: 2016).*
Calabria, D., Dissertation Thesis Date, Implementation of Chemiluminescence and Color-Based Detection in Smartphone For Bioassays, University of Bologna, Apr. 2016, 1-2. (Year: 2016).*
Frank et al., Publication Date, 2019 Papers, International Image Sensor Society, 2019, 1-13. (Year: 2019).*
Frank et al., Image Artifacts in Backside Illumination CMOS Image Sensors Associated with Electrostatic Charge, 2019 Papers of the International Image Sensor Society, 2019, R18, 1-3. (Year: 2019).*
Sobek et al., Analysis of Fluorescent Dyes Used for Labeling DNA in Microarray Experiments, Millipore Sigma, 2021, 1-6. Obtained online at https://www.sigmaaldrich.com/US/en/technical-documents/technical-article/genomics/gene-expression-and-silencing/analyzing-fluorescent-dye-dna-labeling Dec. 30, 2021. (Year: 2021).*

(Continued)

*Primary Examiner* — Amy M Bunker
(74) *Attorney, Agent, or Firm* — Kilpatrick Townsend & Stockton LLP

(57) ABSTRACT

Embodiments of the invention provide an improved biosensor for biological or chemical analysis. According to embodiments of the invention, backside illumination (BSI) complementary metal-oxide-semiconductor (CMOS) image sensors can be used to effectively analyze and measure fluorescence or chemiluminescence of a sample. This measured value can be used to help identify a sample. Embodiments of the invention also provide methods of manufacturing an improved biosensor for biological or chemical analysis and systems and methods of DNA sequencing.

3 Claims, 16 Drawing Sheets

(56) References Cited

U.S. PATENT DOCUMENTS

| | | |
|---|---|---|
| 2012/0224050 A1 | 9/2012 | Staker |
| 2012/0231830 A1 | 9/2012 | Jeong et al. |
| 2012/0261830 A1 | 10/2012 | Chu et al. |
| 2013/0116153 A1 | 5/2013 | Bowen et al. |
| 2013/0293749 A1* | 11/2013 | Vaartstra ............... H04N 9/045 348/273 |
| 2014/0073514 A1 | 3/2014 | Shen et al. |
| 2014/0152801 A1* | 6/2014 | Fine .................. G02B 21/0008 348/79 |
| 2014/0256030 A1 | 9/2014 | Shen et al. |
| 2014/0272719 A1 | 9/2014 | Liu et al. |
| 2014/0376069 A1 | 12/2014 | Reinmuth |
| 2015/0056097 A1 | 2/2015 | Vaartstra |
| 2015/0079596 A1 | 3/2015 | Eltoukhy et al. |
| 2015/0087534 A1 | 3/2015 | Gormley et al. |
| 2015/0177150 A1 | 6/2015 | Rothberg et al. |
| 2015/0177715 A1 | 6/2015 | Smith |
| 2015/0279894 A1 | 10/2015 | Cheng et al. |
| 2016/0061740 A1 | 3/2016 | Grot et al. |
| 2016/0064439 A1 | 3/2016 | Or-Bach et al. |
| 2016/0133517 A1 | 5/2016 | Delamarche et al. |
| 2016/0237488 A1 | 8/2016 | Ke et al. |
| 2016/0338347 A1 | 11/2016 | White et al. |
| 2018/0155782 A1 | 6/2018 | Zhong et al. |
| 2018/0195961 A1 | 7/2018 | Earney et al. |

FOREIGN PATENT DOCUMENTS

| | | | |
|---|---|---|---|
| CN | 103221810 A | | 7/2013 |
| CN | 104372080 A | | 2/2015 |
| CN | 105980580 A | | 9/2016 |
| CN | 105980832 A | | 9/2016 |
| CN | 110506336 A | | 11/2019 |
| EP | 2221606 A2 | | 8/2010 |
| EP | 2362418 A2 | | 8/2011 |
| EP | 2362418 A3 | | 7/2012 |
| EP | 2879181 A1 | | 6/2015 |
| JP | 2001524667 A | | 12/2001 |
| JP | 2004532397 A | | 10/2004 |
| JP | 2006010582 A | | 1/2006 |
| JP | 2007333497 A | | 12/2007 |
| JP | 2009082675 A | | 4/2009 |
| JP | 2009092675 A | | 4/2009 |
| JP | 2010531994 A | | 9/2010 |
| JP | 2011137742 A | | 7/2011 |
| JP | 2011145308 A | | 7/2011 |
| JP | 2011520111 A | | 7/2011 |
| JP | 2013509618 A | | 3/2013 |
| JP | 2013084747 A | | 5/2013 |
| JP | 2013088378 A | | 5/2013 |
| JP | 2013092393 A | | 5/2013 |
| JP | 2015073070 A | | 4/2015 |
| JP | 2015533503 A | | 11/2015 |
| JP | 2017504789 A | | 2/2017 |
| KR | 20040025932 A | | 3/2004 |
| KR | 20100091840 A | | 8/2010 |
| KR | 20160096644 A | | 8/2016 |
| TW | 201231952 A | | 8/2012 |
| TW | I447901 B | | 8/2014 |
| TW | 201629484 A | | 8/2016 |
| TW | 201629486 A | | 8/2016 |
| TW | 201639094 A | | 11/2016 |
| TW | 201732285 A1 | | 9/2017 |
| WO | 2009/001988 A1 | | 12/2008 |
| WO | 2011/103497 A1 | | 8/2011 |
| WO | 2014/031157 A1 | | 2/2014 |
| WO | 2014/077783 A1 | | 5/2014 |
| WO | 2015/089092 A1 | | 6/2015 |
| WO | WO-2015089092 A1 * | 6/2015 | ......... G01N 21/6454 |
| WO | 2016032562 A1 | | 3/2016 |
| WO | 2017026439 A1 | | 2/2017 |
| WO | 2017075344 A1 | | 5/2017 |
| WO | 2018175341 A1 | | 9/2018 |

OTHER PUBLICATIONS

Deetlefs et al., Quill Ionic Liquids, Catalyst, 2014, 1-3. (Year: 2014).*

Kedmi et al., The Systematic Toxicity of Positively Charged Lipid Nanoparticles and the Role of Toll-Like Receptor 4 in Immune Activation, Biomaterials,2010, 31, 6867-6875. (Year: 2010).*

International Search Report and Written Opinion received in International Patent Application No. PCT/US2018/023176, dated Jun. 13, 2018. 13 pages.

International Preliminary Report on Patentability received in International Application No. PCT/US2017/059908, dated May 16, 2019. 9 pages.

International Search Report and Written Opinion received in International Patent Application No. PCT/US2018/050437, filed Sep. 11, 2018. Received Dec. 13, 2018. 14 pages.

International Search Report and Written Opinion received in International Patent Application No. PCT/US2017/059908, filed Nov. 3, 2017. Received Feb. 2, 2018. 18 pages.

Drmanac, R. et al. *Human Genome Sequencing Using Unchained Base Reads on Self-Assembling DNA Nanoarrays.* Science, vol. 327. Published Jan. 1, 2010. pp. 78-81.

Ronaghi, M. et al. *DNA Sequencing: A Sequencing Method Based on Real-Time Pyrophosphate.* Science, vol. 281, Issue 2375. Published Jul. 17, 1998. pp. 363-365.

Shendure, J. et al. *Next-Generation DNA Sequencing.* Nature Biotechnology, vol. 26, Issue 10. Published Oct. 2008. pp. 1135-1145.

Application 17867617.7, Extended European Search Report, May, 25, 2020, 11 Pages.

Application PCT/US2018/050437—International Preliminary Report on Patentability and Written Opinion, Apr. 2, 2020, 9 pages.

Seitz et al., "Chemiluminescence and Bioluminescence", Analytical Chemistry, Feb. 1974, pp. 188-202, vol. 46, No. 2.

EP18857916.3 , "Extended European Search Report", May 7, 2021, 9 pages.

Supplementary European Search Report for Application No. 18 77 0661, mailed Dec. 16, 2020, 12 pages.

Arkles, B., "Hydrophobicity, Hydrophilicity and Silanes", *Paint & Coatings Industry*, Jan. 1, 2006, 10 pages, retrieved from the Internet on Jan. 8, 2013 at URL:http://www.gelest.com/goods/pdf/Library/advances/HydrophobicityHydrophilictyandSilanes.pdf.

* cited by examiner

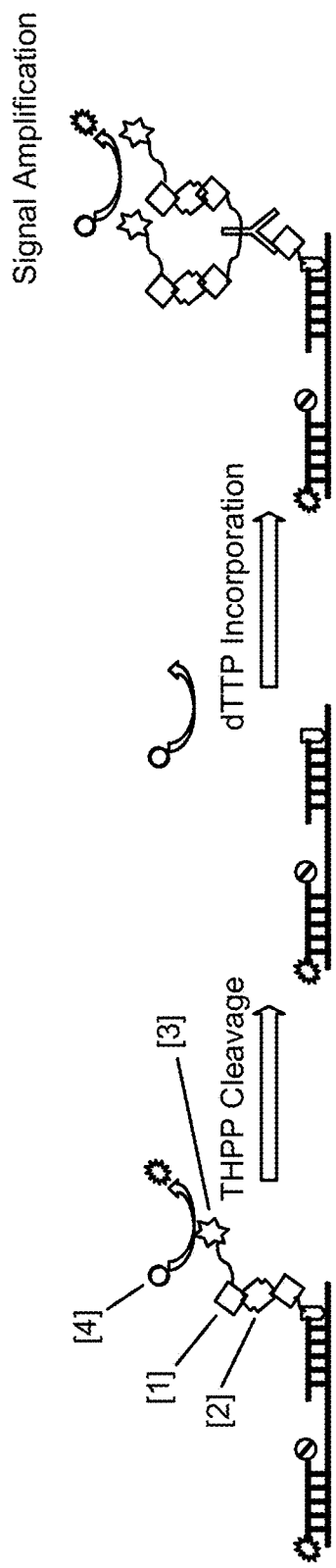
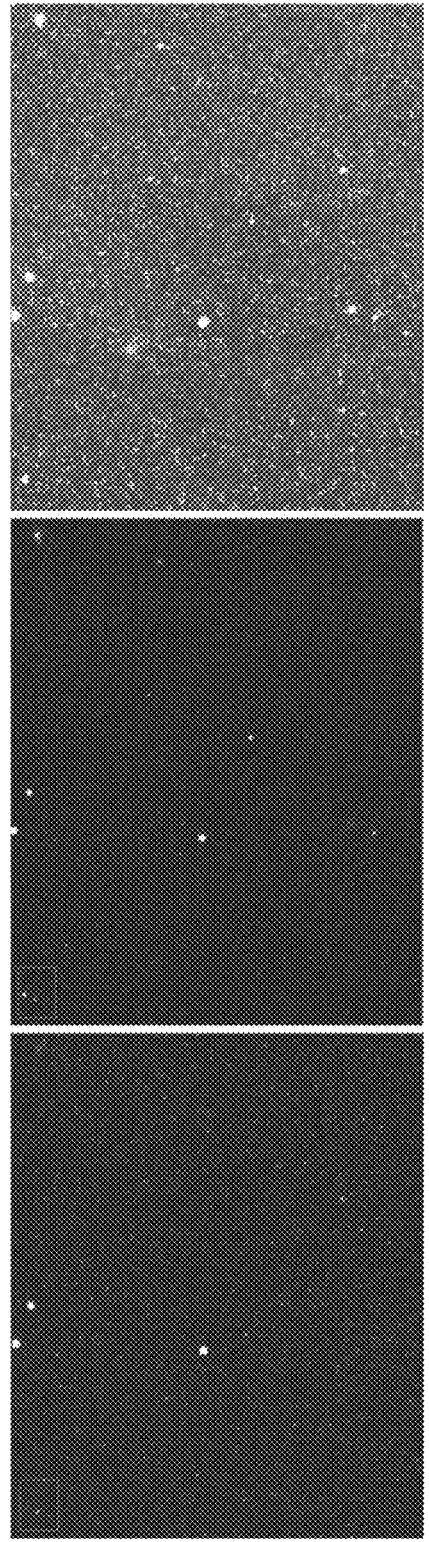
FIG. 15A  FIG. 15B  FIG. 15C

BIOSENSORS FOR BIOLOGICAL OR CHEMICAL ANALYSIS AND METHODS OF MANUFACTURING THE SAME

CROSS-REFERENCES TO RELATED APPLICATIONS

This application claims priority to U.S. Provisional Patent Application No. 62/416,813, filed Nov. 3, 2016, the content of which is incorporated by reference in its entirety.

FIELD

The present invention relates generally to a biosensor for biological or chemical analysis, and more specifically, to a biosensor including a backside illumination (BSI) complementary metal-oxide-semiconductor (CMOS) image sensor and methods of manufacturing the same.

BACKGROUND OF THE INVENTION

CMOS image sensors find use in electronic imaging devices, including digital cameras, medical imaging equipment, radar devices, and the like. Using integrated circuits and a series of photodiodes, CMOS image sensors can capture light and convert it into electrical signals.

CMOS image sensors are typically implemented on chips. The chips may have an amplifier for each pixel. Although the inclusion of many amplifiers in a chip may result in less area for the capture of light, other components can be integrated onto the chip to direct more light into the photodiodes. For example, microlenses may be placed in front of the photodiodes to direct light into the photodiodes. To further increase the amount of light that hits the photodiodes, backside illumination (BSI) can be used. BSI effectively places the photodiodes closer to the light source, instead of under and between the integrated circuit wiring, reducing destructive interference. BSI CMOS sensors also have other advantages. For example, BSI CMOS sensors may have low operating voltage, low power consumption, high efficiency, and low noise.

BSI CMOS image sensors typically have two functional areas: a light sensing area and an electronic circuit area. The light sensing area includes the photodiodes arranged in an array, coupled to metal-oxide-semiconductor (MOS) transistors that detect the light intensity. The electronic circuit area provides connections between the MOS transistors and external connections, such as to other devices for processing the data from the MOS transistors.

In practice, a BSI CMOS image sensor employs filters that divide incident light into bands of light of different wavelengths. The light is received by the photodiodes on a substrate and transformed into electrical signals of different intensity. For example, an incident beam may be divided into red, green, and blue light and received by respective photodiodes for each color. Each photodiode transforms the detected light intensity into electrical signals. This is accomplished by the photodiode accumulating a charge. For example, the higher the intensity of the light, the higher the charge accumulated in the photodiode. The accumulated charge can then be correlated to a color and brightness.

In addition to the uses described above, CMOS image sensors may also be used for biological or chemical analysis. For such analysis, a biological or chemical sample may be placed above a photodiode, and light emitted by the biological or chemical sample may be directed to the photodiode. The fluorescence or chemiluminescence of the sample can be detected by the photodiode, and a color and brightness can be determined. This color and brightness may be used to identify the biological or chemical sample.

SUMMARY OF THE INVENTION

Embodiments of the invention address the drawbacks associated with previous approaches by providing an improved biosensor for biological or chemical analysis. According to embodiments of the invention, BSI CMOS image sensors can be used to effectively analyze and measure fluorescence or chemiluminescence of a sample. This measured value can be used to help identify a sample. Embodiments of the invention also provide methods of manufacturing an improved biosensor for biological or chemical analysis. As used herein, the term "biosensor" may be used to refer to an apparatus for determining a light emitting substance within or attached to a biological molecule, particularly a nucleic acid macromolecule exemplified by DNA and branched or otherwise derivatized nucleic acids. As used herein, the term "nucleic acid macromolecule" may refer to, for example, DNB or single strand embodiments.

According to some embodiments of the invention, a biosensor is provided. The biosensor comprises a backside illumination complementary metal-oxide-semiconductor (CMOS) image sensor. The backside illumination CMOS image sensor includes an electronic circuit layer and a photo sensing layer over the electronic circuit layer. The photo sensing layer includes a substrate layer and a photodiode in contact with the electronic circuit layer. A light receiving surface is defined by a surface of the photodiode opposite to the electronic circuit layer. The biosensor further comprises a color filter material over the photodiode. The biosensor further comprises a spot or well above the color filter material that is sized and functionalized to receive a nucleic acid macromolecule, and to absorb light from the nucleic acid macromolecule or to pass the light to the light receiving surface from the nucleic acid macromolecule.

A method of manufacture according to some embodiments comprises providing a backside illumination complementary metal-oxide-semiconductor (CMOS) image sensor. Providing the backside illumination CMOS image sensor includes providing an electronic circuit layer and providing a photo sensing layer over the electronic circuit layer. The photo sensing layer includes a substrate layer and a photodiode in contact with the electronic circuit layer. A light receiving surface is defined by a surface of the photodiode opposite to the electronic circuit layer. The method further comprises depositing a color filter material over the photodiode. The method further comprises providing a spot or well above the color filter material that is sized and functionalized to receive a nucleic acid macromolecule, and to absorb light from the nucleic acid macromolecule or to pass light to the light receiving surface from the nucleic acid macromolecule.

A method of DNA sequencing according to some embodiments comprises iteratively performing a process that may include labeling a nucleic acid macromolecule with a fluorescent label that identifies a nucleotide base at a particular position in the nucleic acid macromolecule. The process further includes detecting the fluorescent label associated with the nucleic acid macromolecule. Detecting the fluorescent label includes illuminating the nucleic acid macromolecule with excitation light. The nucleic acid macromolecule absorbs the excitation light and transmits emitted light through a color filter and onto a photodiode of a backside illumination complementary metal-oxide-semiconductor (CMOS) image sensor. Detecting the fluorescent label further includes measuring at least one parameter of the emitted light received at the photodiode. Detecting the fluorescent or chemiluminescent label further includes correlating the at least one parameter of the emitted light to the fluorescent label. The process further includes removing the fluorescent label from the nucleic acid macromolecule. Without limitation, the biosensors of embodiments of the invention may be used to carry out sequencing-by-synthesis (SBS), sequencing-by-ligation, cPAL sequencing, pyrosequencing, and combinations of the foregoing.

The foregoing, together with other features and embodiments, will become more apparent upon referring to the following specification, claims, and accompanying drawings.

BRIEF DESCRIPTION OF THE DRAWINGS

Illustrative embodiments of the present invention are described in detail below with reference to the following drawing figures:

FIGS. 15A-15C are photographic images showing signals from DNBs at numerous spots on the array in a BSI CMOS chip at various stages of a multiple step sequencing according to some embodiments.

DETAILED DESCRIPTION OF THE INVENTION

Figure 1:
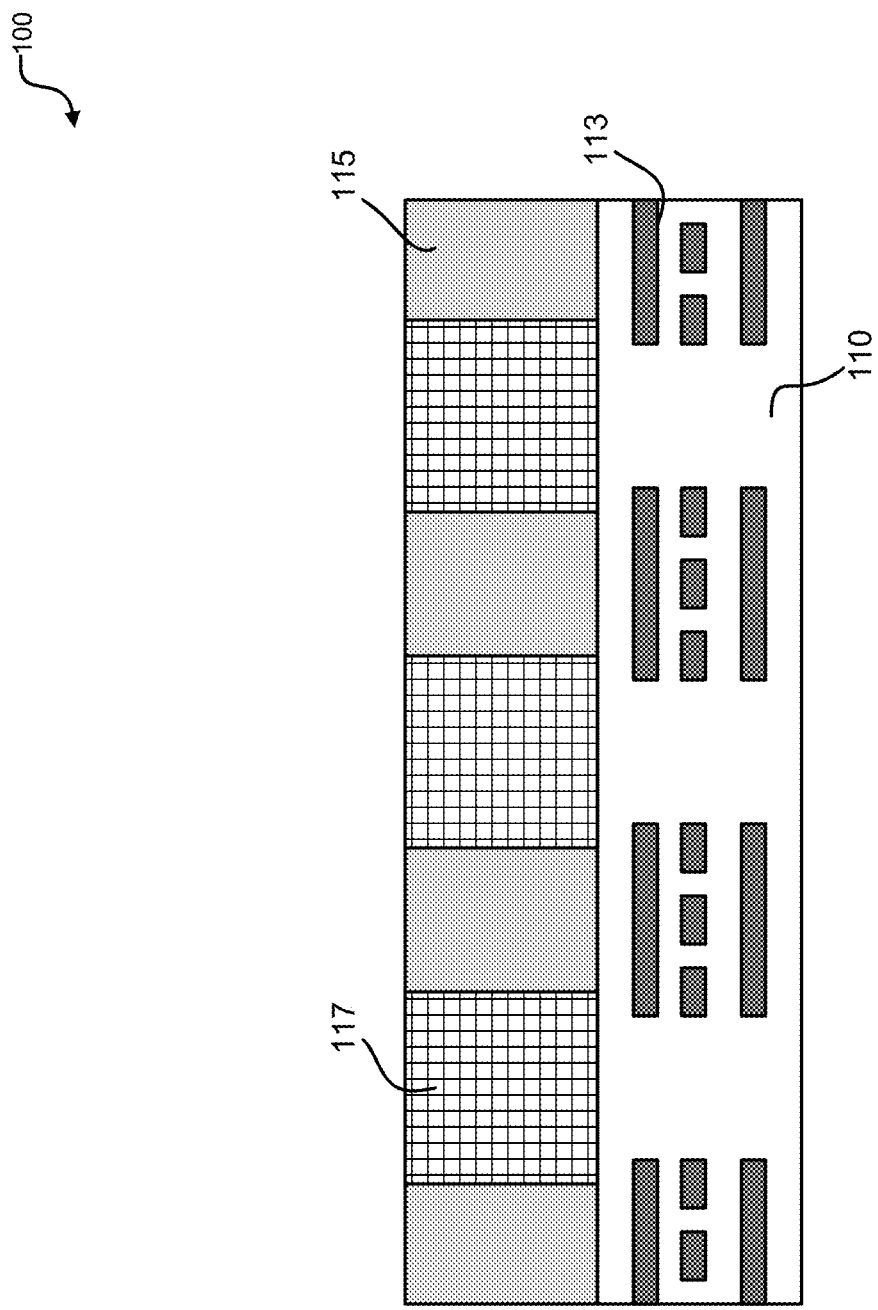
FIG. 1 is a cross-sectional view of a backside illumination CMOS image sensor, according to some embodiments

FIGS. 1-13 describe various stages of manufacture of a biosensor according to embodiments of the invention. Other embodiments of manufacture and configuration will be evident from this description to those of skill in the art. It is therefore intended that the following description be descriptive but not limiting.

For ease of reading, the text below is organized into sections. However, it will be understood that a description of subject matter in one section (e.g., descriptions of macromolecules, filters, sequencing methods, etc.) may also apply to subject matter in other sections.

Biosensors according to embodiments of the invention are not limited to a particular use. In one aspect, the biosensors of embodiments of the invention find particular use for massively parallel DNA sequencing. DNA sequencing technologies are well known (see, e.g., Drmanac et al., 2010, "Human genome sequencing using unchained base reads on self-assembling DNA nanoarrays," *Science* 327:78-81; Shendure & Ji, 2008, "Next-generation DNA sequencing," *Nature Biotechnology* 26:1135-45) and are therefore described only in general terms in sections below. The following paragraphs provide a brief initial discussion of sequencing and associated terminology so that certain features of the biosensors described below may be more easily understood.

A variety of DNA sequencing methods are known. In many approaches, large molecules (e.g., genomic DNA) are broken into many smaller fragments, each having a characteristic DNA sequence. In array based technologies, the fragments are distributed to an array of positions on a substrate so that each position in the array contains a DNA fragment with a single characteristic sequence. Sequence information ("reads") is obtained from DNAs at each of thousands, or more often, millions, of positions simultaneously and assembled by a computer. In most sequencing approaches, the fragments are amplified prior to sequence determination. The amplification may occur prior to the positioning of the fragments at each position, after the positioning of the fragments at each position, or both before and after positioning. The amplification step(s) produce "amplicons" which serve as "templates" in a sequencing process. Thus, for illustration, amplification may use RCA to produce a single-stranded concatemer (e.g., a DNA nanoball) at each position on the array or use bridge PCR to produce a clonal population (or cluster) of DNA molecules with the same sequence at each position.

It will be understood that reference to a "DNA macromolecule," and the like, encompasses DNA nanoballs, branched structures, and clustered clonal populations (i.e., more than a single molecule) or their precursors. In addition, a "DNA macromolecule," and the like, may encompass auxiliary DNA molecules such as primers and growing strands produced by primer extension or other processes encompasses. In many sequencing technologies, it is the auxiliary DNA molecules that comprise (or are "labeled" with) a detectable (e.g., fluorescent or chemiluminescent) dye that emit light detected by photodiodes of the biosensor. Thus, a phrase such as "illuminating the nucleic acid macromolecule with an excitation light source and detecting light emitted from the macromolecule" will be understood to encompass "exposing a DNA nanoball or clonal cluster and associated labeled auxiliary molecules with an excitation light source and detecting light emitted from the dyes of the labeled auxiliary molecules."

In array-based sequencing methods, and the biosensors of embodiments of the invention, DNA macromolecules are positioned on a substrate in wells or on "spots." The wells or spots are able to receive and retain the macromolecule. Often, the spots, sometimes called "discrete spaced apart regions" or "pads", comprise a substrate functionalized to receive a nucleic acid macromolecule and the spots are separated by areas that are "inert" in the sense that DNA macromolecules do not bind such areas. For example, and without limitation, see Drmanac 2010, supra. "Wells" are a type of spot comprising walls that form a boundary or barrier to the DNA macromolecules. Except where clear from context, reference to "spots" below may include wells.

In biosensors of embodiments of the invention, spots generally have uniform dimensions and are organized as a regular (i.e., not random) array. The spots of an array are generally organized in a rectilinear pattern, often in columns and rows, but other regular patterns may be used (e.g., a spiral). The spots of an array may have characteristic dimensions, pitch, and density. The spots themselves may be circular, square, hexagonal or other shape. In the discussion below, the spots are generally assumed to be circular (i.e., can be described as having a diameter). It will be understood that reference to a "diameter" can also refer to linear dimensions of other shaped spots (e.g., diagonal, length or width). Thus, as used herein, "linear dimension" can refer to a diameter of a circle, width of a square, diagonal, and the like. In the context of biosensors of embodiments of the invention, the size of the spots is meaningful in two ways. First, the spots may be sized and/or functionalized in a way that limits occupancy to a single target sequence. This may be a single DNA nanoball (a concatemer of a single target sequence) or a clonal cluster with a single target sequence. See, e.g., U.S. Pat. No. 8,133,719 and U.S. Pat. App. Pub. No. 2013/0116153, both incorporated by reference in their entireties for all purposes. Secondly, generally the spots may be sized and positioned relative to underlying photodiodes so that each photodiode receives emitted light from a single spot. In some embodiments, an array of spots may be positioned over an array of corresponding photodiode(s) (and/or color filters) with a 1 to 1 correlation. That is, light emitted from an, e.g., DNA macromolecule at individual spot passes into an underlying filter and light not blocked by the filter is detected by a single photodiode associated with the filter, or light emitted from an, e.g., DNA macromolecule, at individual spot passes into a plurality of underlying filters, each associated with a filter (specific for particular wavelengths), each associated with a single photodiode, and light not blocked by a filter is detected by the associated photodiode. Thus, as also discussed below, in some embodiments, light emitted from a single spot may be detected by more than one photodiode (e.g., 2, 3, 4, etc.) photodiodes. In these embodiments, a group of multiple photodiodes associated with a single spot may be referred to as a "unit cell" of photodiodes. The spots and filters (e.g., single filters or unit cells) may be arranged in the biosensor such that each photodiode in the unit cell receives light emitted from the same single spot. In addition, in some embodiments, the area of the light receiving surface of a photodiode, or combined area of the light receiving surfaces of multiple photodiodes associated with the same spot, is less than the area of the spot (from which light is emitted). Put another way, the spot may be smaller than the underlying photodiode(s) such that the boundary of the spot, if projected onto the light receiving surface of the photodiode(s), is contained within the light receiving surface.

As is well known, nucleic acid sequencing generally involves an iterative process in which a fluorescent or chemiluminescent label is associated in a sequence in a specific way with the DNA template (amplicon) being sequenced, the association is detected, and the label is removed in the sense that it no longer emits a signal. See, e.g., U.S. Pat. App. Pub. No. 2016/0237488; U.S. Pat. App. Pub. No. 2012/0224050; U.S. Pat. Nos. 8,133,719; 7,910, 354; 9,222,132; 6,210,891; 6,828,100, 6,833,246; and 6,911, 345, herein incorporated by reference in their entireties. Thus it will be appreciated that, for example, "labeling a nucleic acid macromolecule with a fluorescent label" may refer to associating a labeled auxiliary molecule(s) with a DNA template immobilized on a spot.

Turning now to the drawings, FIG. 1 is a cross-sectional view of a backside illumination (BSI) CMOS image sensor 100 according to some embodiments. The BSI CMOS image sensor 100 may include a first dielectric layer 110. Although described as being dielectric, it is contemplated that the first dielectric layer 110 may include any suitable electrically insulating material. The first dielectric layer 100 may include metal wiring 113. The metal wiring 113 may include integrated circuit materials and external connections. Together, the first dielectric layer 100 and the metal wiring 113 may be collectively referred to herein as an "electronic circuit layer" of the BSI CMOS image sensor.

A substrate layer 115 may be provided over the first dielectric layer 110 and the metal wiring 113. The substrate layer 115 may be made of any suitable material, such as, for example, silicon, III-V group on silicon, graphene-on-silicon, silicon-on-insulator, combinations thereof, and the like. The substrate layer 115 may include openings in which light sensing components (e.g., photodiodes 117) may be positioned. Although described herein with respect to photodiodes 117, it is contemplated that any suitable light sensing component may be used. The photodiodes 117 may be configured to convert measured light into current. Photodiodes 117 may include the source and drain of a MOS transistor (not shown) that may transfer the current to other components, such as other MOS transistors. The other components may include a reset transistor, a current source follower or a row selector for transforming the current into digital signals, and the like. Together, the substrate layer 115 and the photodiodes 117 may be collectively referred to herein as a "photo sensing layer" of the BSI CMOS image sensor.

The photodiodes 117 may be in contact with metal wiring 113 to communicate the digital signals to external connections via the metal wiring 113. In the BSI CMOS image sensor 100 illustrated in FIG. 1, the light receiving surface is positioned at the top of the photodiodes 117 (i.e., on a surface not in contact with the electronic circuit layer and opposite to the electronic circuit layer), and incident light is received by the photodiodes 117 at this light receiving surface.

Figure 2:
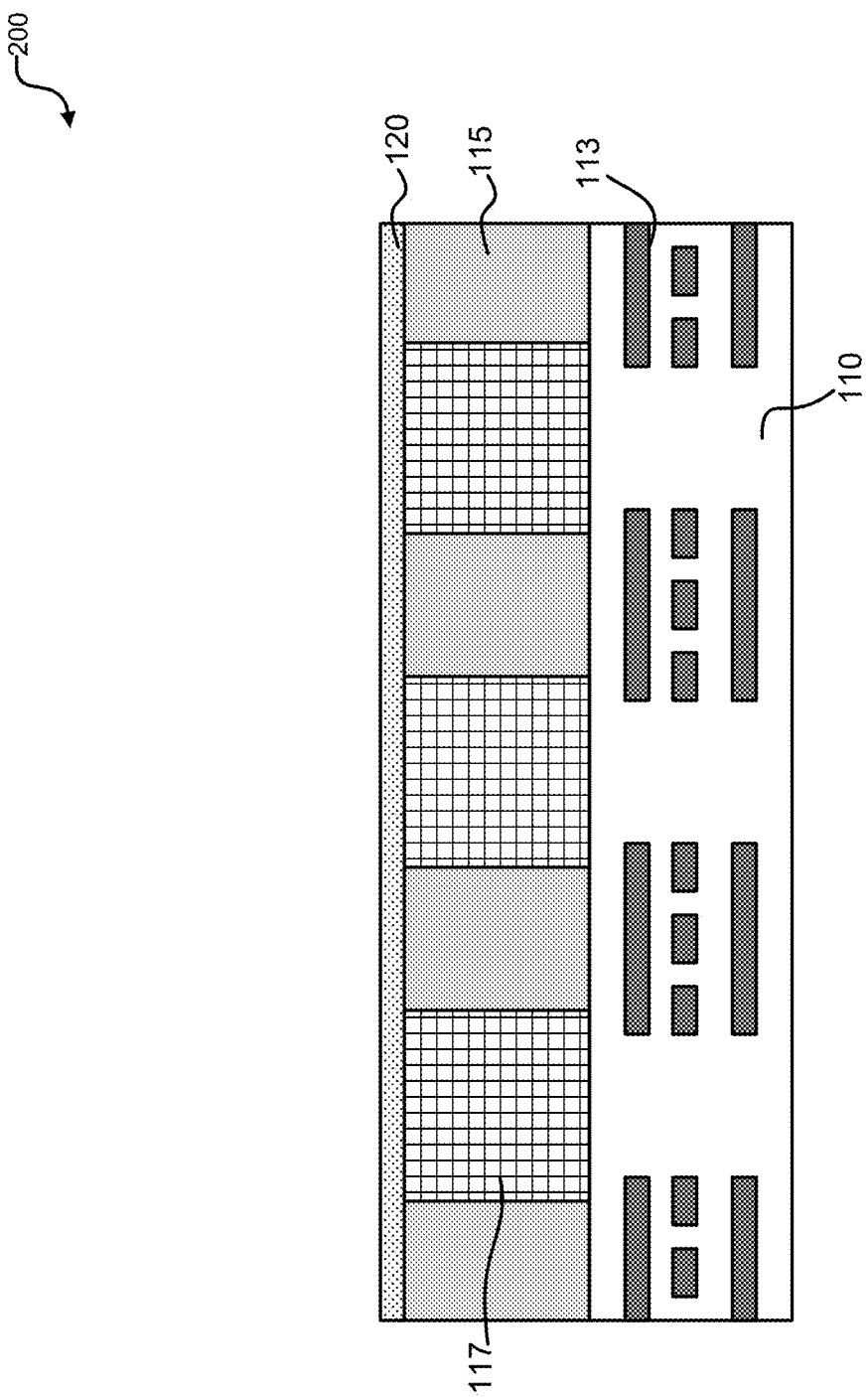
FIG. 2 is a cross-sectional view of a backside illumination CMOS image sensor with a first passivation layer, according to some embodiments.
Figure 3:
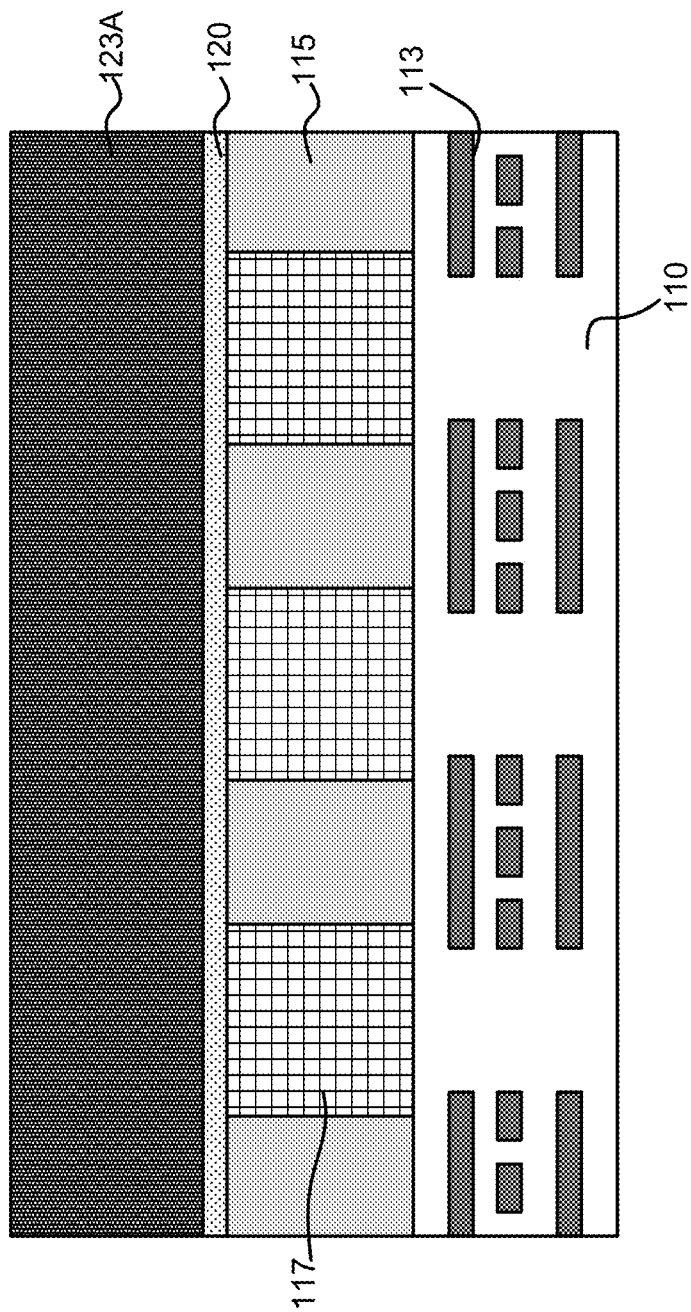
FIG. 3 is a cross-sectional view of a backside illumination CMOS image sensor with a first metal layer, according to some embodiments.

According to FIG. 2, in order to construct a biosensor 200, a first passivation layer 120 may be deposited by conventional semiconductor processing techniques (e.g., low temperature plasma chemical vapor deposition) on the substrate layer 115 and the photodiodes 117 of the BSI CMOS image sensor 100. The first passivation layer 120 may include any suitable protective material. For example, the first passivation layer 120 may include materials such as silicon, oxide, metals, combinations thereof, and the like. The first passivation layer 120 may act as an etch stop for later etching steps, as described further herein. The first passivation layer 120 may alternatively or additionally act to protect the active device (i.e., the backside illumination CMOS sensor). The first passivation layer 120 may alternatively or additionally act to protect photodiodes 117 from wear caused by frequent use. The first passivation layer 120 may be transparent. In one example, the first passivation layer 120 may have a thickness of 100 nanometers or less.

A. Biosensor 200 of FIG. 2

FIG. 2 illustrates a biosensor 200 that may be used for biological or chemical analysis (e.g., to detect the chemiluminescence of a macromolecule or macromolecular complex), according to some embodiments. The biosensor 200 includes a backside illumination CMOS image sensor 100. The backside illumination CMOS image sensor 100 includes an electronic circuit layer (comprised of the first dielectric layer 110 and the metal wiring 113) and a photo sensing layer over the electronic circuit layer (comprised of a substrate layer 115 and photodiodes 117). The photodiodes 117 may be in contact with the electronic circuit layer such that electronic signals may be transmitted from the photodiode 117 to the electronic circuit layer, and in some embodiments, to an external device. A light receiving surface is defined by a surface of the photodiodes 117 that is opposite to the electronic circuit layer (i.e., the surface in contact with the first passivation layer 120).

The biosensor 200 may further include the first passivation layer 120 over the backside illumination CMOS image sensor 100, and spots or wells (not shown) formed over or in the first passivation layer 120 on or over which chemical or biological samples may be placed for analysis. In some embodiments, the biosensor 200 may be adapted for detecting an optical signal (e.g., fluorescent or chemiluminescent emission) from a corresponding array of biomolecules, where individual biomolecules may be positioned over (e.g., in spots or wells) one or more photodiodes such that the one or more photodiodes receive light from the biomolecule, as discussed in greater detail below.

Various further embodiments for constructing biosensors using a backside illumination CMOS sensor 100 may now be described. According to FIG. 3, a first metal layer 123A may be deposited by conventional semiconductor processing techniques on the first passivation layer 120 of biosensor 200 (e.g., by metal deposition techniques). The first metal layer 123A may include any suitable metal material. For example, the first metal layer 123A may include materials such as tungsten, aluminum, gold, copper, combinations or alloys thereof, and the like. In some embodiments, the first metal layer 123A may be a thick layer, e.g., thicker than the first passivation layer 120. For example, the first metal layer 123A may be up to 3 micrometers.

Figure 4:
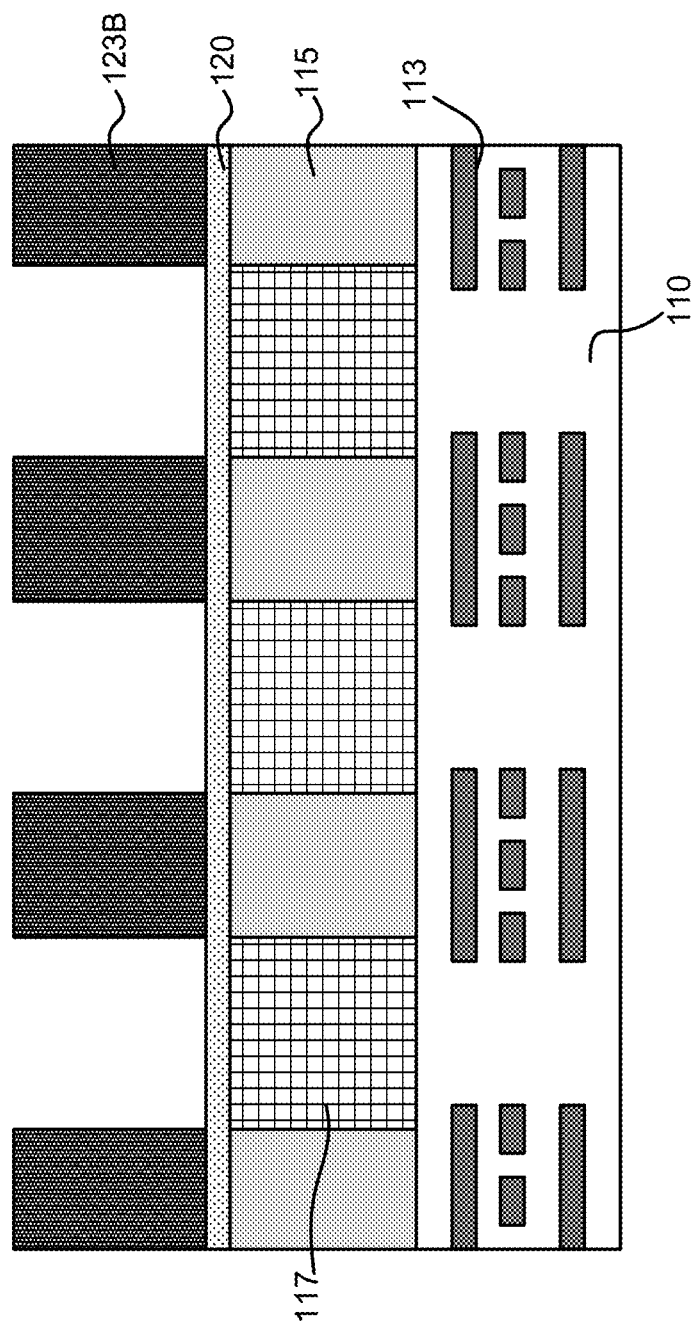
FIG. 4 is a cross-sectional view of a backside illumination CMOS image sensor with an etched first metal layer, according to some embodiments.

According to FIG. 4, the first metal layer 123A may be etched to provide first openings above the photodiodes 117, leaving first metal layer 123B. The first metal layer 123A may be etched by any suitable process, such as, for example, wet etching, dry etching, combinations thereof, and the like. It is contemplated that etching the first metal layer 123A may involve use of a mask, for example. The etching may be completed using any of a variety of materials, such as, for example, acids (e.g., hydrochloric acid, hydrofluoric acid, nitric acid, etc.), alkali with oxidizers, combinations thereof, and the like. It is contemplated that the type of acid needed to etch the first metal layer 123A may depend on the material used for forming the first metal layer 123A. In some embodiments, the first openings may be aligned center to center with the photodiodes 117, maximizing efficiency of the photodiodes 117 in later use. A mask (not shown) may define the openings over the photodiodes 117, leaving first metal layer 123B remaining, and the first passivation layer 120 may act as an etch stop when etching the openings in the first metal layer 123A. As described herein, the pillars of the first metal layer 123B may separate light received by separate color filters and may reflect back light intended for a certain color filter back into that color filter or into the corresponding photodiode 117.

Figure 5:
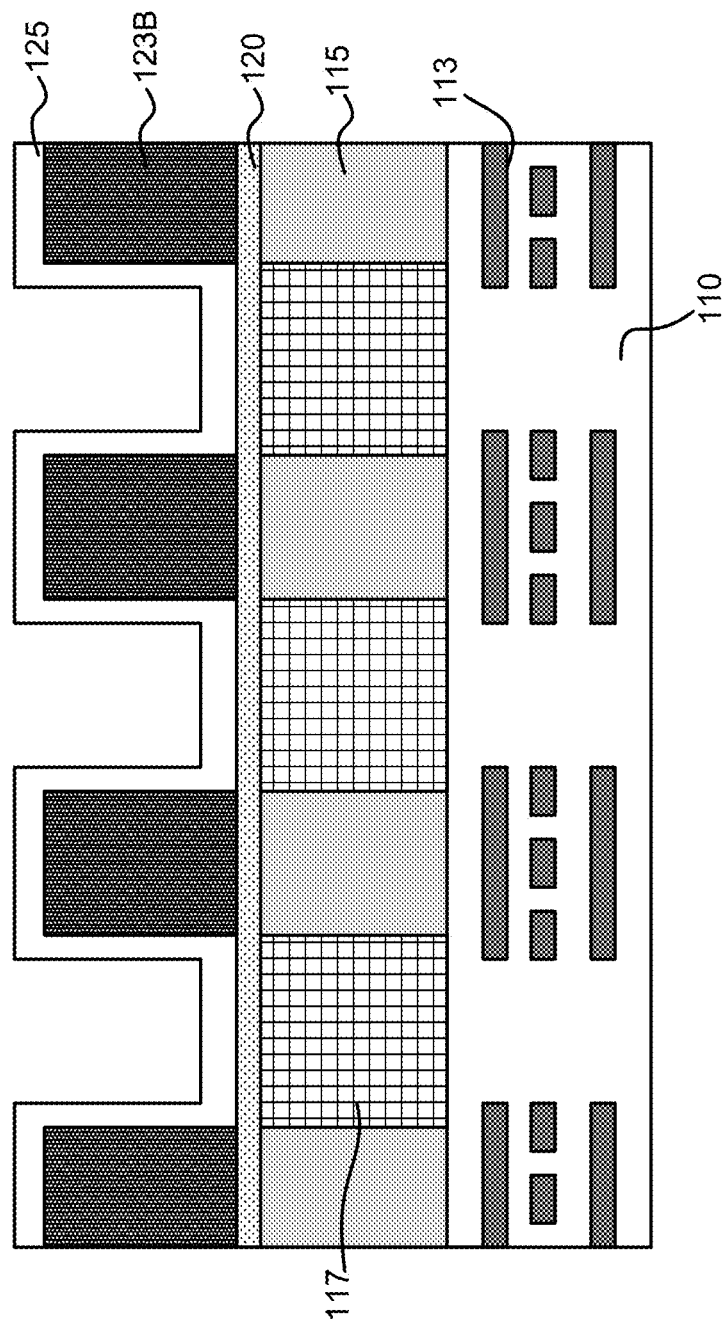
FIG. 5 is a cross-sectional view of a backside illumination CMOS image sensor with a dielectric layer, according to some embodiments.

According to FIG. 5, a second dielectric layer 125 may be deposited over the first metal layer 123B and in the first openings by conventional semiconductor processing techniques. In some embodiments, the second dielectric layer 125 may be formed on all exposed sides of the first metal layer 123B. Although described as being dielectric, it is contemplated that the second dielectric layer 125 may include any suitable electrically insulating material, such as silicon nitride, tantalum oxide, combinations thereof, and the like. The second dielectric layer 125 may be formed of a same or different material than the first dielectric layer 110.

Figure 6:
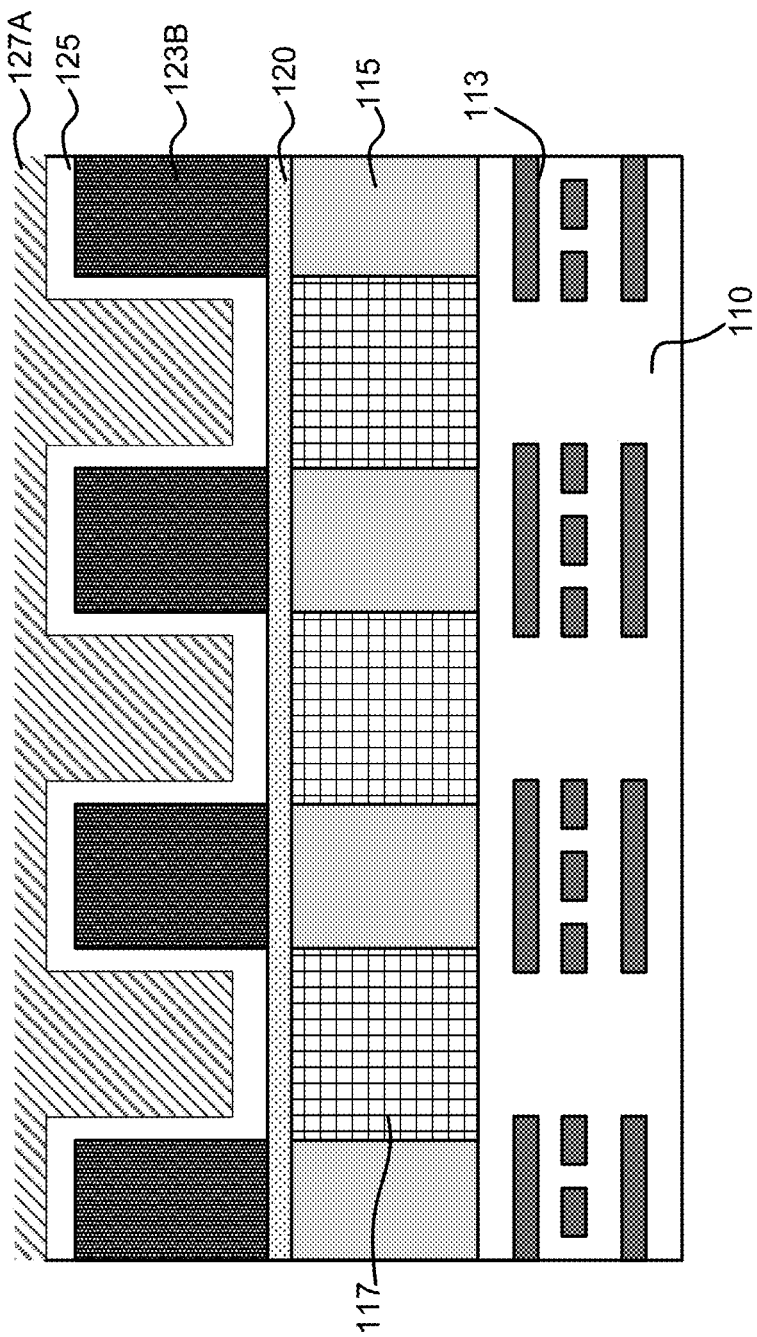
FIG. 6 is a cross-sectional view of a backside illumination CMOS image sensor with a color filter layer, according to some embodiments.
Figure 7:
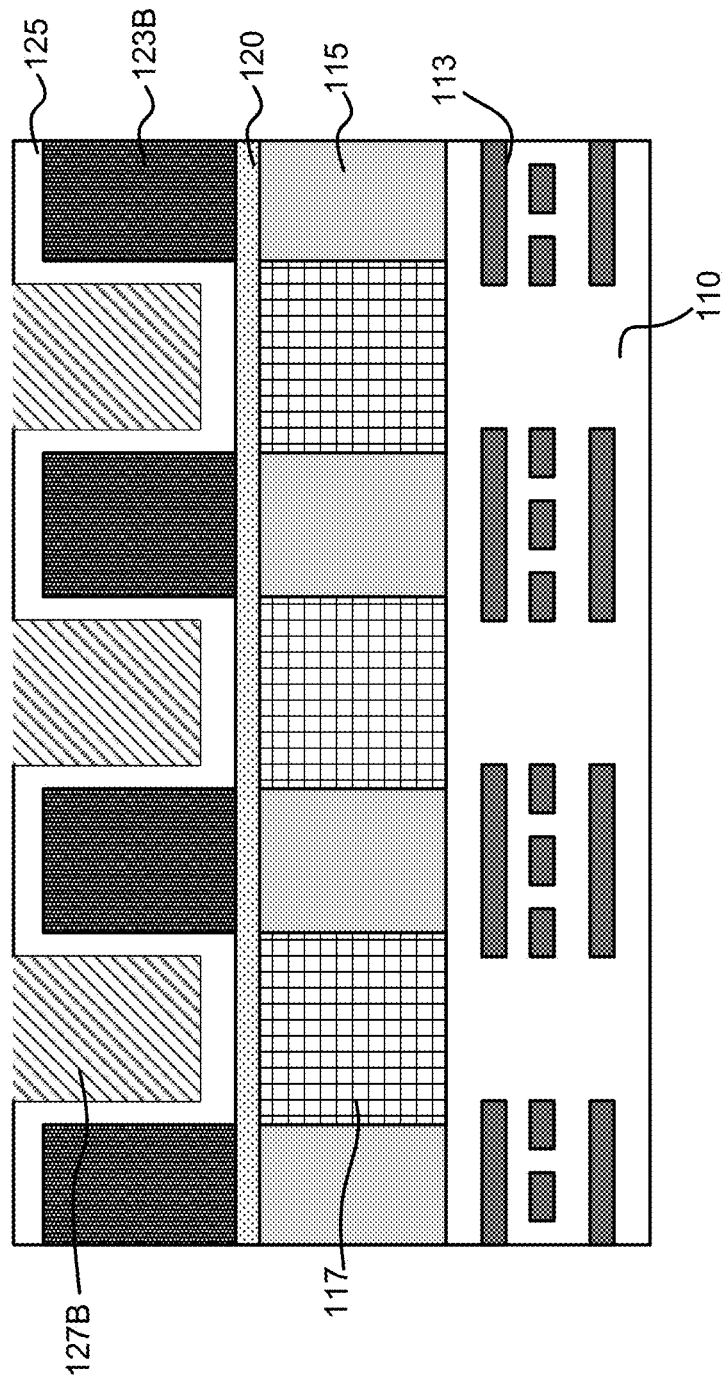
FIG. 7 is a cross-sectional view of a backside illumination CMOS image sensor with a planarized color filter layer, according to some embodiments.

According to FIG. 6, color filter material 127A may be deposited over the second dielectric layer 125. In some embodiments, color filter material 127A may be deposited by spin coating. Color filter material 127A fills the openings created by second dielectric layer 125. In this embodiment, color filter material 127A is also deposited on the portions of second dielectric layer 125 between the openings. Thus, according to FIG. 7, the excess color filter material 127A above the openings of the second dielectric layer 125 may be removed, such as by, for example, chemical-mechanical planarization (CMP), leaving color filter material 127B in the openings of the second dielectric layer 125.

However, it is also contemplated that in some embodiments, the process shown in FIG. 6 may be omitted. In other words, as in FIG. 7, color filter material 127B may be selectively deposited only in the openings of the second dielectric layer 125, such that more than one (e.g., 2, 3 or 4) different color filter material 127B may be placed above the photodiodes 117. In some applications, each different color filter material 127B may be associated with a separate photodiode 117.

The color filter material 127B may include, for example, a pigment-based polymer, a pigment-based dye, a dye-based polymer, a resin or other organic based material, combinations thereof, and the like. Color filter material 127B may be necessary for the biosensor, for example, because the photodiodes 117 may alone detect light intensity with little or no wavelength specificity, and thus cannot separate color information.

Color filter material 127B may include blue filter material, red filter material, green filter material, emerald filter material, cyan filter material, yellow filter material, magenta filter material, white filter material, combinations thereof, and the like. Thus, the color filter material 127B may filter incident light by wavelength range, such that the separate filtered intensities include information about the color of light. For example, red color filter material 127B may give information about the intensity of light in red wavelength regions. Blue color filter material 127B may give information about the intensity of light in blue wavelength regions.

Green color filter material 127B may give information about the intensity of light in green wavelength regions, and so on and so forth.

Figure 14B:
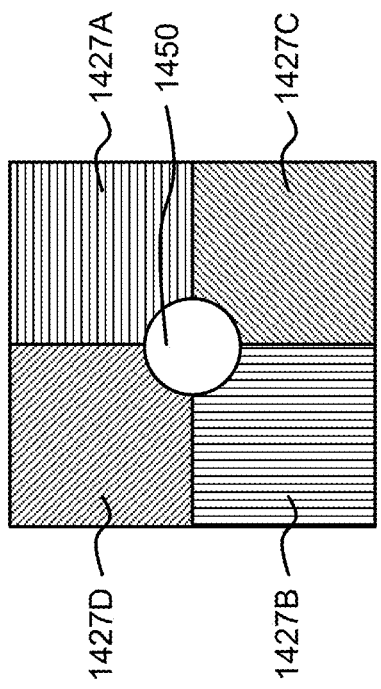
FIG. 14B is a top view of a four-channel color filter that may be used in a biosensor, according to some embodiments.
Figure 14A:
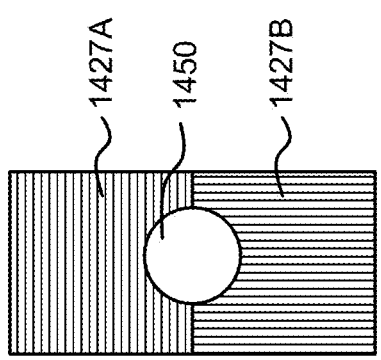
FIG. 14A is a top view of a two-channel color filter that may be used in a biosensor, according to some embodiments.

In some embodiments, color filter material 127B may include material of a single color. For example, each of the color filter materials 127B may be red. In some embodiments, color filter material 127B may include material of different colors, with each color filter material 127B corresponding to a separate photodiode 117. For example, one color filter material 127B may be red, and a neighboring color filter material 127B may be green. FIG. 14A illustrates such an embodiment, in which a two-channel color filter is used. In FIG. 14A, a biological or chemical sample (e.g., a DNA macromolecule) may be positioned in a spot or well 1450 such that emissions from the macromolecule enter both the red color filter material 1427B and the green color filter material 1427A (e.g., overlapping both the red color filter material 1427B and the green color filter material 1427A), and such that the emitted wavelength of light through the different colors of the color filter material may be detected. In another example, more than two surrounding color filter materials 127B may include material of different colors. FIG. 14B illustrates such an embodiment, in which a four-channel color filter is used. The four-channel color filter may include one color filter material 1427B that is red, one color filter material 1427D that is yellow, one color filter material 1427A that is green, and one color filter material 1427C that is blue. In this example, a biological or chemical sample may be placed in a spot or well 1450 at the intersection of the four color filters, such that the emitted wavelength of light through the four colors of the color filter material may be detected. In some embodiments, spot or well 1450 may lie above each of the underlying color filter materials (and corresponding photodiodes) equally, i.e., so that equal areas of each filter underlies the spot.

Figure 8A:
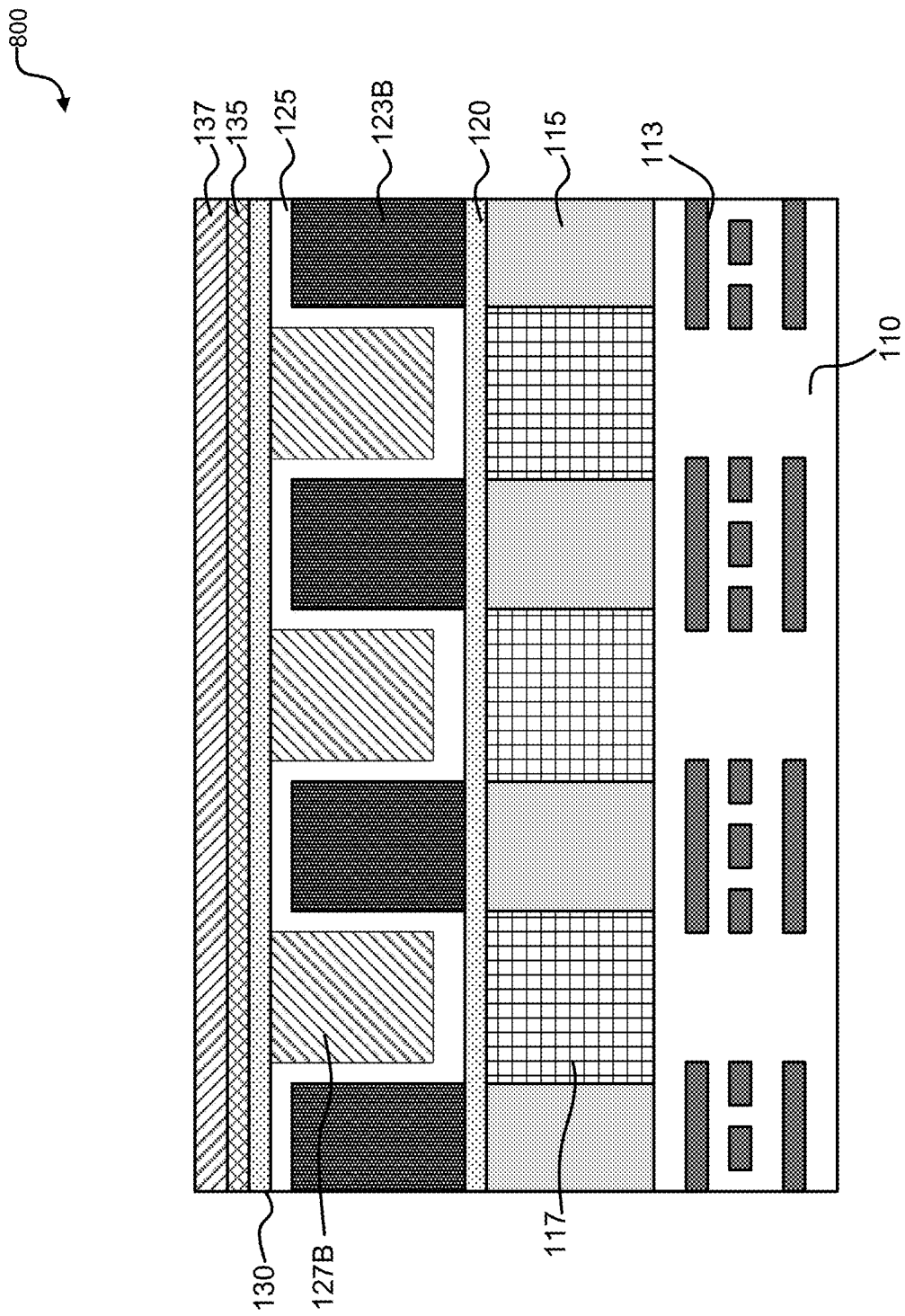
FIG. 8A is a cross-sectional view of a backside illumination CMOS image sensor with a second passivation layer, a first material layer, and a second metal layer, according to some embodiments.

FIG. 8A illustrates an embodiment in which biosensor 800 is constructed. According to FIG. 8A, the second passivation layer 130 may be deposited according to conventional semiconductor techniques over the second dielectric layer 125 and the color filter material 127B. The second passivation layer 130 may be as described below with respect to FIG. 8B. A first material layer 135 may be deposited over the second passivation layer 130. The first material layer 135 may include any suitable materials, such as silicon nitride, tantalum oxide, combinations thereof, and the like. A second material layer 137 may be deposited over the first material layer 135. The second material layer 137 may include any suitable materials, such as silicon dioxide and the like. In some embodiments, the first material layer 135 may have a refractive index that is higher than the refractive index of the second material layer 137. In some embodiments, the first material layer 135 may have a refractive index that is higher than the second passivation layer 130. Thus, the embodiment of FIG. 8A may result in efficient delivery of excitation light to the light receiving surface in the case of fluorescence measurement. For example, the first material layer 135 may form the core of an optical waveguide, thus permitting low loss transmission of excitation light. In some embodiments, biological or chemical samples may be placed on the second material layer 137 above the photodiodes 117 (in some embodiments, in openings or wells formed on the second material layer 137), and their fluorescence or chemiluminescence may be measured by the photodiodes 117, as described further herein. When measuring fluorescence in the embodiment shown in FIG. 8A, however, the excitation light may be directed sideways, along the surface of the biosensor 800, in some examples.

B. Biosensor 800 of FIG. 8A

Thus, FIG. 8A illustrates a biosensor 800 that may be used for biological or chemical analysis according to some embodiments. The biosensor 800 may include a backside illumination CMOS image sensor 100. The backside illumination CMOS image sensor 100 includes an electronic circuit layer (comprised of the first dielectric layer 110 and the metal wiring 113) and a photo sensing layer over the electronic circuit layer (comprised of a substrate layer 115 and photodiodes 117). The photodiodes 117 may be in contact with the electronic circuit layer such that electronic signals may be transmitted from the photodiode 117 to the electronic circuit layer, and in some embodiments, to an external device. A light receiving surface is defined by a surface of the photodiodes 117 that is opposite to the electronic circuit layer (i.e., the surface in contact with the first passivation layer 120).

The biosensor 800 may further include the first passivation layer 120 over the backside illumination CMOS image sensor 100, and a first metal layer 123B over the first passivation layer 120. The first metal layer 123B may also be positioned over substrate layer 115. The first metal layer 123B may include first openings. The biosensor 800 may further include a second dielectric layer 125 over the metal layer 123B and the first passivation layer 120. The second dielectric layer 125 may also be positioned in the first openings of metal layer 123B.

The biosensor 800 may further include color filter material 127B over the second dielectric layer 125 and in and above the first openings of metal layer 123B, such that a top surface of color filter material 127B may be planar with a top surface of the second dielectric layer 125 over the metal layer 123B. The biosensor 800 may further include a second passivation layer 130 over the second dielectric layer 125 and the color filter material 127. The biosensor 800 may further include a first material layer 135 and a second material layer 137. The first material layer 135 may have a higher refractive index than the second material layer 137. A biological or chemical sample may be placed in spots or wells (not shown) formed in or on the second material layer 137 for analysis, as described further herein.

Figure 8B:
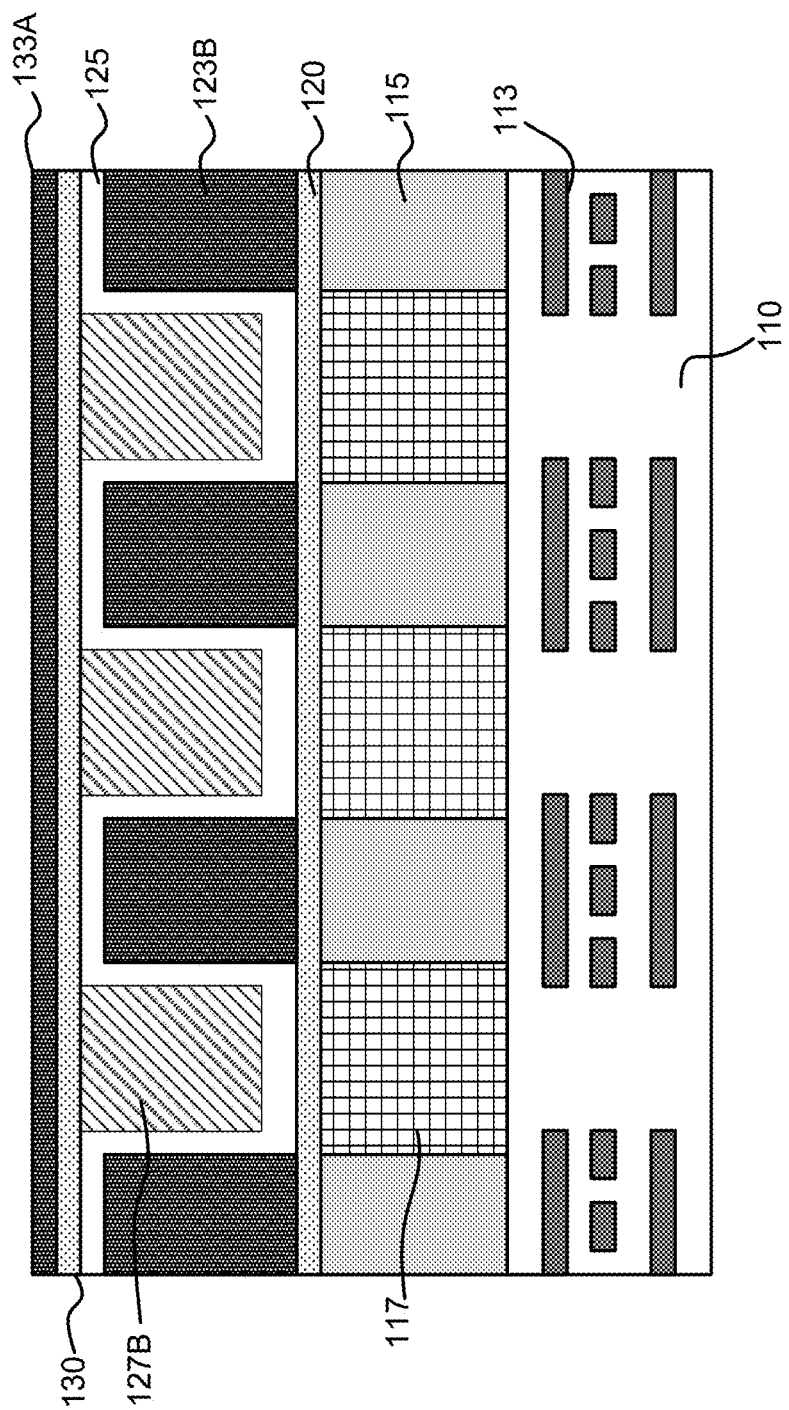
FIG. 8B is a cross-sectional view of a backside illumination CMOS image sensor with a second passivation layer and a second metal layer, according to some embodiments.

FIG. 8B illustrates an alternative embodiment than FIG. 8A. According to FIG. 8B, a second passivation layer 130 may be deposited according to conventional semiconductor techniques over the second dielectric layer 125 and the color filter material 127B. The second passivation layer 130 may include any suitable materials, such as, for example, silicon nitride, tantalum oxide, combinations thereof, and the like. In some embodiments, the second passivation layer 130 may include one or more high-k materials. The second passivation layer 130 may include the same or different materials than the first passivation layer 120. In some embodiments, the second passivation layer 130 is made of a denser material than the first passivation layer 120. The second passivation layer 130 may, in some embodiments, act as a protective material between a sample being analyzed and the color filter material 127B. In some embodiments, the second passivation layer 130 acts as an etch stop for later etching steps. The second passivation layer 130 may be transparent.

Further according to FIG. 8B, a second metal layer 133A may be deposited according to conventional semiconductor techniques over the second passivation layer 130. The second metal layer 133A may include any suitable metal material, such as, for example, tungsten, aluminum, copper, combinations thereof, and the like. The second metal layer 133A may be made of the same or a different material than the first metal layer 123B. The second metal layer 133A may be opaque to incident or excitation light.

Figure 9:
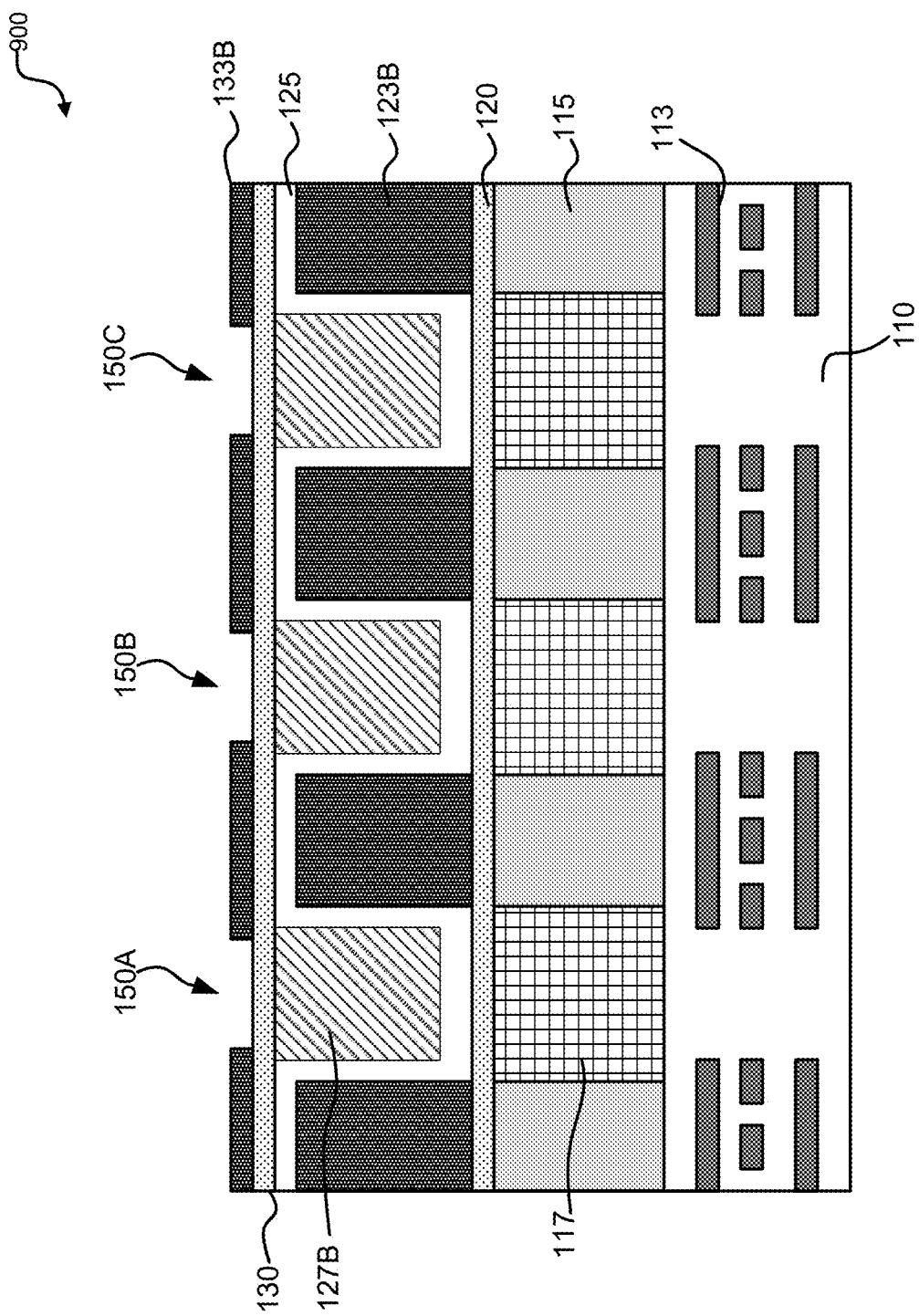
FIG. 9 is a cross-sectional view of a biosensor using a backside illumination CMOS image sensor, according to some embodiments.
Figure 10:
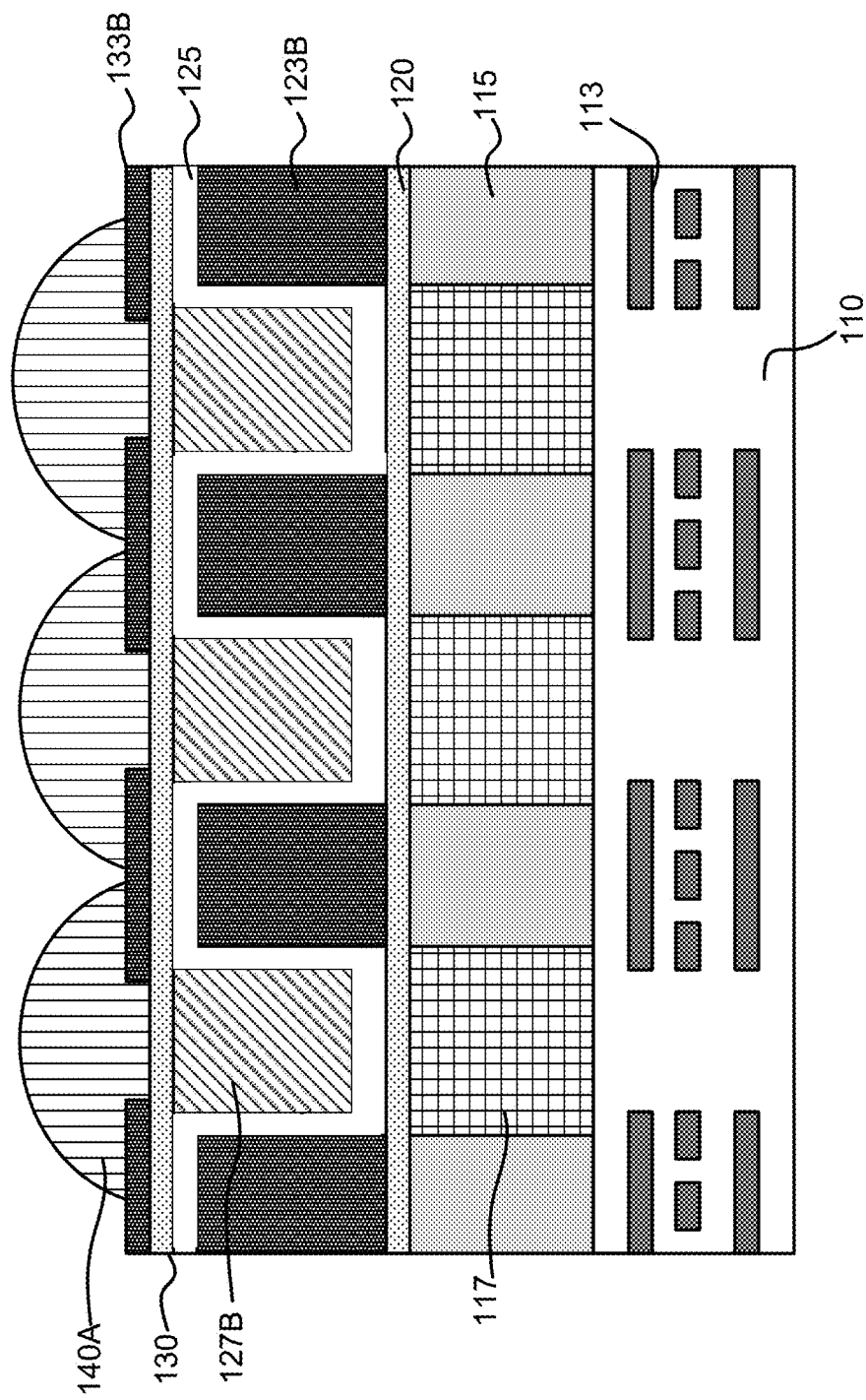
FIG. 10 is a cross-sectional view of a biosensor using a backside illumination CMOS image sensor and microlenses, according to some embodiments.

Then, according to FIG. 9, the second metal layer 133B may be etched out of the second metal layer 133A or patterned, creating second openings 150A-C in the second metal layer 133A. In some embodiments, the second openings 150A-C may be aligned center to center with the photodiodes 117. In some embodiments, the second openings 150A-C may have a diameter in the range of 100 nanometer to 1 micrometer. The second openings 150A-C may have a smaller width or diameter than the color filter material 127B. In some embodiments, biological or chemical samples may be placed in the second openings 150A-C, and light emitted from the samples may be used to measure their fluorescence or chemiluminescence, as described further herein. In embodiments in which the second openings 150A-C are smaller in width or diameter than the color filter material 127B, there may be increased blockage of incident or excitation light, resulting in less noise in detection of the fluorescence or luminescence of a sample. The width or diameter of the second openings 150A-C may approximately correspond to the size of the biological or chemical sample being analyzed.

C. Biosensor 900 of FIG. 9

Thus, FIG. 9 illustrates a biosensor 900 that may be used for biological or chemical analysis according to some embodiments. The biosensor 900 includes a backside illumination CMOS image sensor 100. The backside illumination CMOS image sensor 100 includes an electronic circuit layer (comprised of the first dielectric layer 110 and the metal wiring 113) and a photo sensing layer over the electronic circuit layer (comprised of a substrate layer 115 and photodiodes 117). The photodiodes 117 may be in contact with the electronic circuit layer such that electronic signals may be transmitted from the photodiode 117 to the electronic circuit layer, and in some embodiments, to an external device. A light receiving surface is defined by a surface of the photodiodes 117 that is opposite to the electronic circuit layer (i.e., the surface in contact with the first passivation layer 120).

The biosensor 900 may further include the first passivation layer 120 over the backside illumination CMOS image sensor 100, and a first metal layer 123B over the first passivation layer 120. The first metal layer 123B may also be positioned over substrate layer 115. The first metal layer 123B may include first openings. The biosensor 900 may further include a second dielectric layer 125 over the metal layer 123B and the first passivation layer 120. The second dielectric layer 125 may also be positioned in the first openings of metal layer 123B.

The biosensor 900 may further include color filter material 127B over the second dielectric layer 125 and in and above the first openings of metal layer 123B, such that a top surface of color filter material 127B may be planar with a top surface of the second dielectric layer 125 over the metal layer 123B. The biosensor 900 may further include a second passivation layer 130 over the second dielectric layer 125 and the color filter material 127. The biosensor 900 may further include a second metal layer 133B having second openings 150A-C. The second openings 150A-C may function as spots or wells configured to receive biological or chemical samples, as described further herein.

Referring again to the embodiment of FIG. 9, various further manufacturing techniques may be implemented for further signal enhancement, as described herein with respect to FIGS. 10-13. According to FIG. 10, microlenses 140A may be grown over the second passivation layer 130 and the second metal layer 133B. In some embodiments, the microlenses 140A may be aligned center to center with the photodiodes 117. The microlenses 140A may include a variety of materials, such as glass, polymers, plastics, combinations thereof, and the like. The microlenses 140A may be included in the device above each of the color filters 127B to focus light emitted into each of the color filters 127B.

The microlenses 140A may be grown according to any suitable microlens fabrication process, such as those commonly used with respect to CMOS image sensors. As one example, photolithography may be performed on a photoresist or ultraviolet curable epoxy material and the material may be melted to form arrays of microlenses 140A. As another example, small filaments of glass may be melted, and the surface tension of the molten glass may form smooth spherical surfaces. The spherically-surfaced glass may then be mounted and grinded as appropriate to form microlenses 140A. In still another example, wafer-level optics (WLO) may be used, in which multiple lens wafers are precision aligned, bonded together, and diced to form multi-element stacks that may be used as microlenses 140A.

Figure 11:
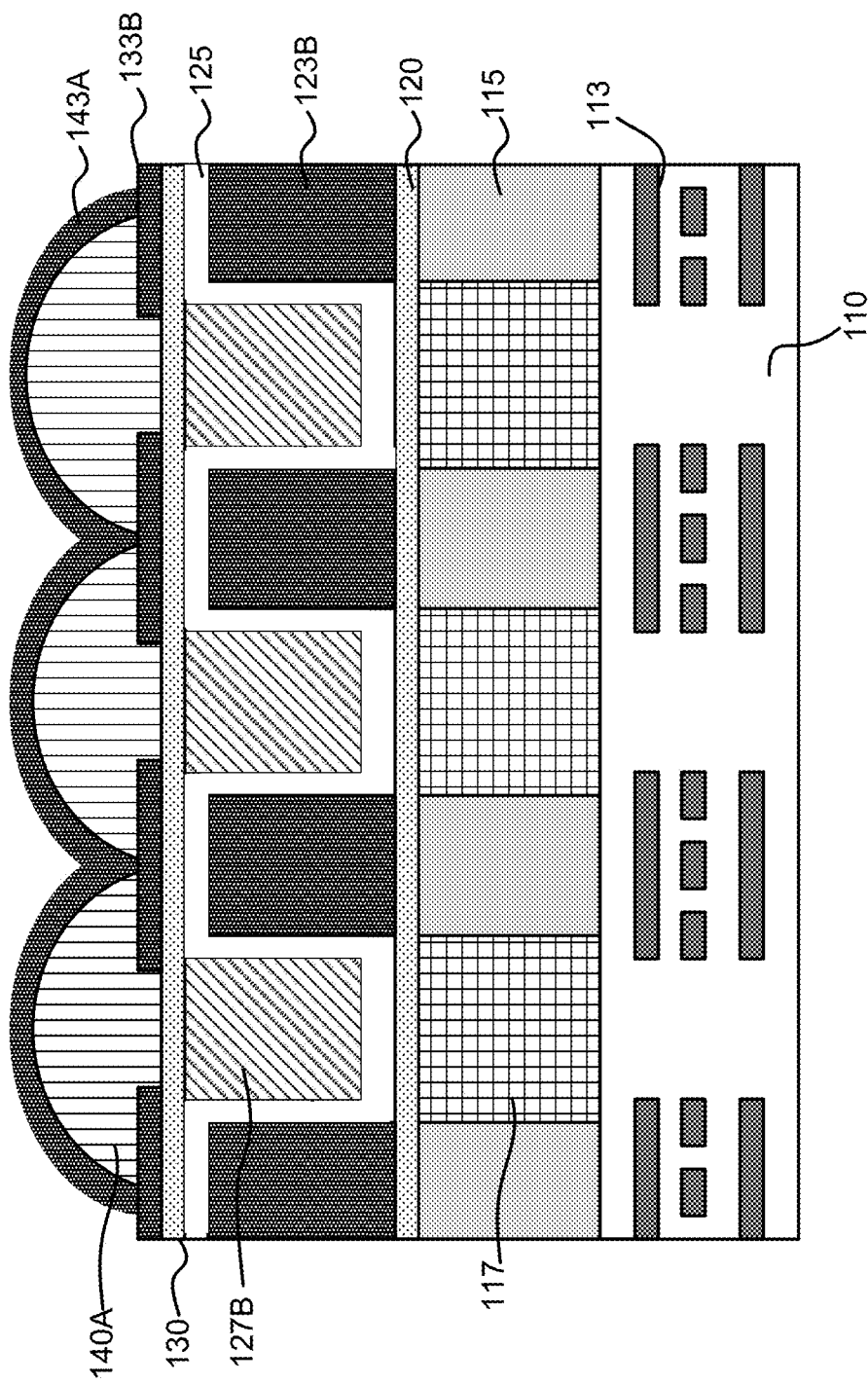
FIG. 11 is a cross-sectional view of a biosensor using a backside illumination CMOS image sensor, microlenses and a third metal layer, according to some embodiments.

According to FIG. 11, a third metal layer 143A may be deposited according to conventional semiconductor processing techniques over the microlenses 140A. The third metal layer 143A may include any suitable materials, such as tungsten, aluminum, copper, combinations thereof, and the like. The third metal layer 143A may be a relatively thin layer, e.g., thinner than the second metal layer 123B. The third metal layer 143A may be made of the same or different materials than the first metal layer 123B and/or the second metal layer 133B.

Figure 12:
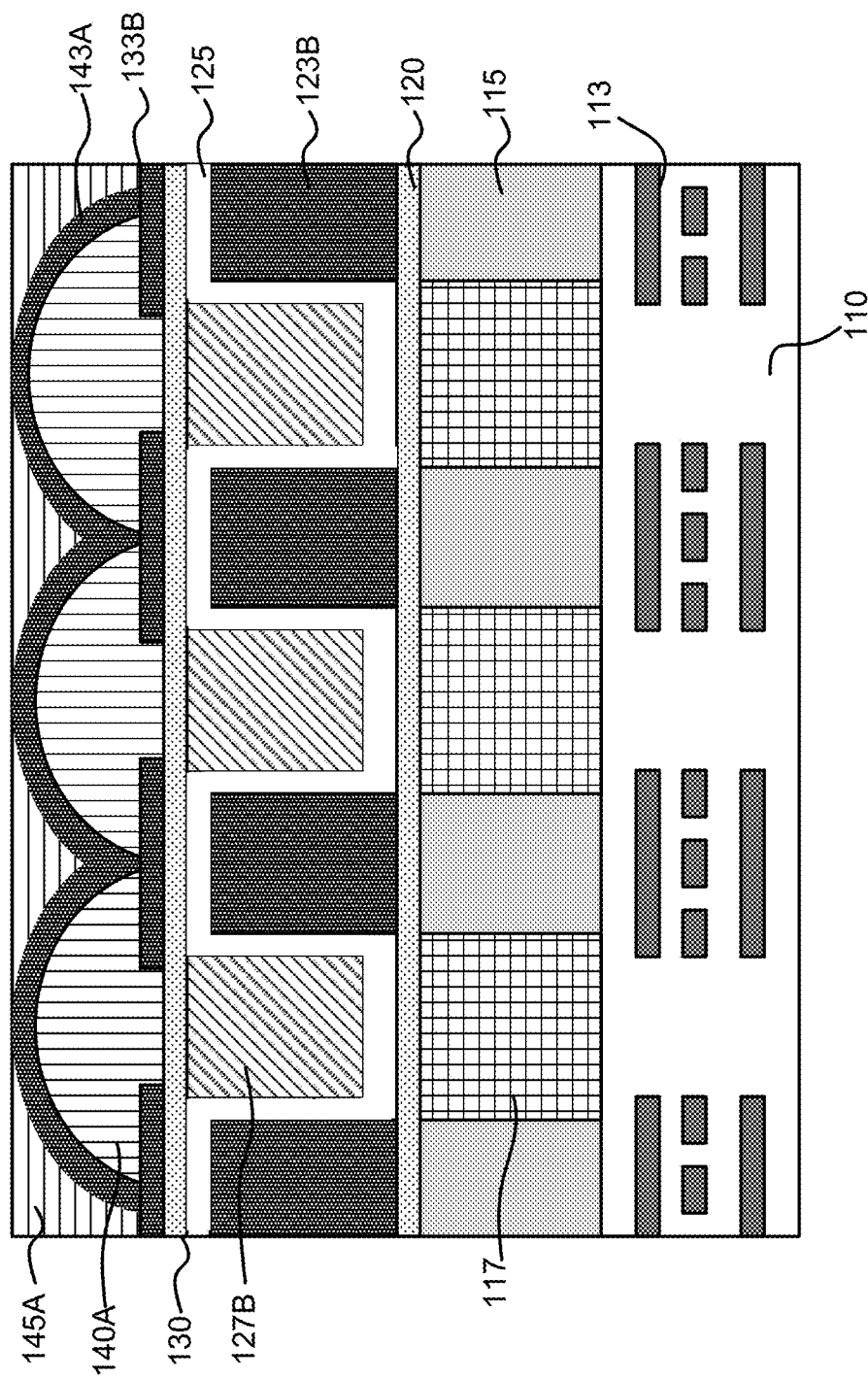
FIG. 12 is a cross-sectional view of a biosensor using a backside illumination CMOS image sensor, microlenses, a third metal layer, and a planarization layer, according to some embodiments.

According to FIG. 12, a planarization layer 145A may be deposited over the third metal layer 143A. The planarization layer 145A may include any suitable materials. The planarization layer 145A may be deposited by, for example, spin coating, or by any other suitable method. If the planarization layer 145A exceeds a top exposed surface of the third metal layer 143A, the planarization layer 145A may be planarized by, for example, chemical-mechanical planarization (CMP), leaving the planarization layer 145A in the openings between the third metal layer 143A and creating a substantially planar upper surface.

Figure 13:
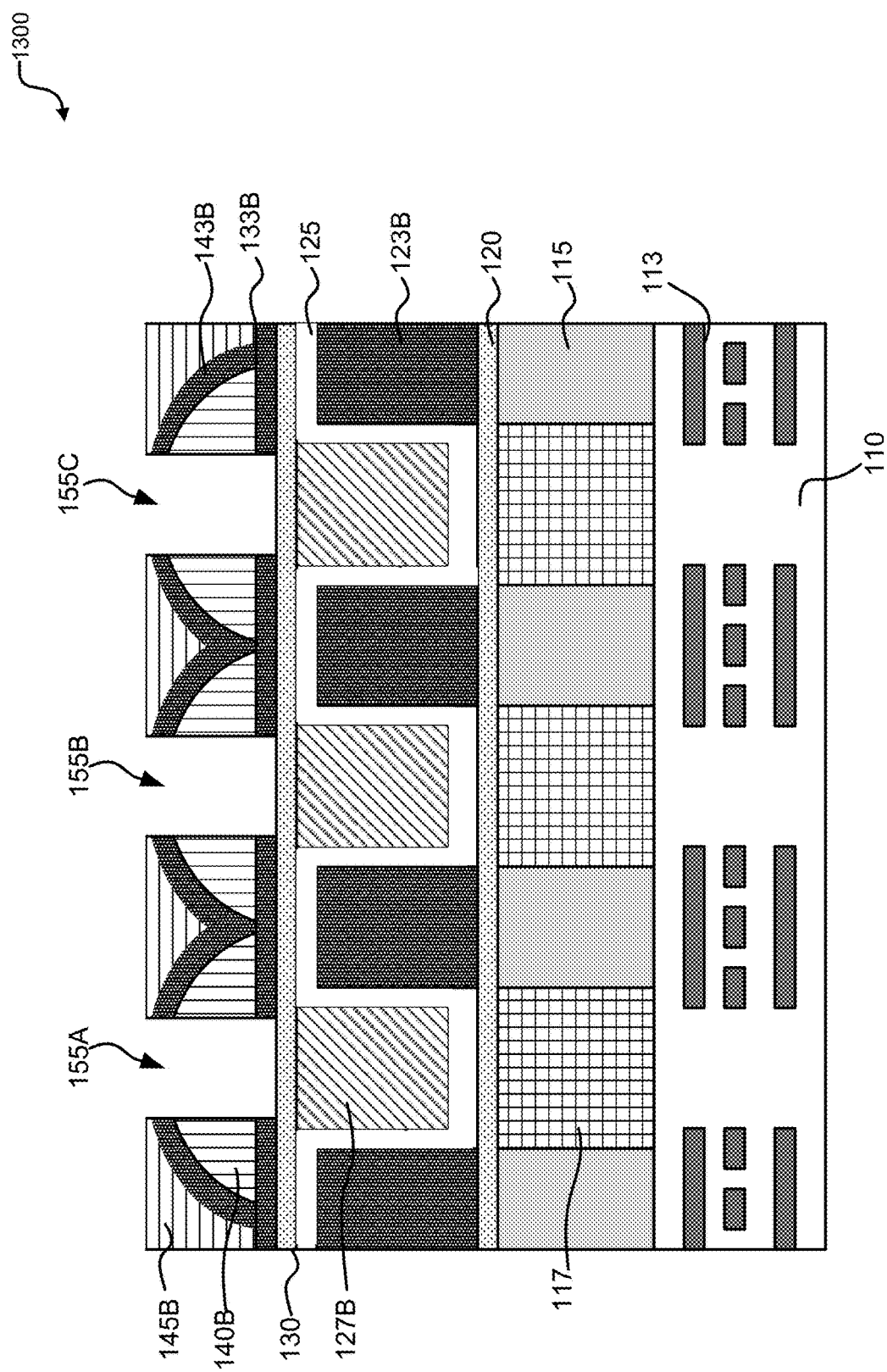
FIG. 13 is a cross-sectional view of a biosensor using a backside illumination CMOS image sensor, according to some embodiments.

According to FIG. 13, third openings 155A-C may be etched through planarization layer 145A (leaving planarization layer 145B remaining), the third metal layer 143A (leaving the third metal layer 143B remaining), and microlenses 140A (leaving the microlenses 140B remaining). For example, the planarization layer 145B may be spin coated with a photoresist (not shown) in order to etch the third openings 155A-C. In some embodiments, the width of the third openings 155A-C may correspond to the width of the second openings 150A-C, such that the second metal layer 133B does not need to be further etched. Third openings 155A-C may be etched to the second passivation layer 130, with the second passivation layer 130 acting as an etch stop. In some examples, third openings 155A-C may have a diameter between 100 nanometers and 1 micrometer, and may be aligned center to center with the color filter material 127B and/or the photodiode 117. In some embodiments, biological or chemical samples may be placed in the third openings 155A-C on the second passivation layer 130, and the fluorescence or chemiluminescence of the samples may be measured, as described further herein.

D. Biosensor 1300 of FIG. 13

Thus, FIG. 13 illustrates a biosensor 1300 that may be used for biological or chemical analysis according to some embodiments. The biosensor 1300 includes a backside illumination CMOS image sensor 100. The backside illumination CMOS image sensor 100 includes an electronic circuit layer (comprised of the first dielectric layer 110 and the metal wiring 113) and a photo sensing layer over the electronic circuit layer (comprised of a substrate layer 115 and photodiodes 117). The photodiodes 117 may be in contact with the electronic circuit layer such that electronic signals may be transmitted from the photodiode 117 to the electronic circuit layer, and in some embodiments, to an external device. A light receiving surface is defined by a surface of the photodiodes 117 that is opposite to the electronic circuit layer (i.e., the surface in contact with the first passivation layer 120).

The biosensor 1300 may further include the first passivation layer 120 over the backside illumination CMOS image sensor 100, and a first metal layer 123B over the first passivation layer 120. The first metal layer 123B may also be positioned over substrate layer 115. The first metal layer 123B may include first openings. The biosensor 1300 may further include a second dielectric layer 125 over the metal layer 123B and the first passivation layer 120. The second dielectric layer 125 may also be positioned in the first openings of metal layer 123B.

The biosensor 1300 may further include color filter material 127B over the second dielectric layer 125 and in and above the first openings of metal layer 123B, such that a top surface of color filter material 127B may be planar with a top surface of the second dielectric layer 125 over the metal layer 123B. The biosensor 1300 may further include a second passivation layer 130 over the second dielectric layer 125 and the color filter material 127. The biosensor 1300 may further include a second metal layer 133B over the second passivation layer 130 having second openings 150A-C.

The biosensor 1300 may further include microlenses 140B over the second metal layer 133B, a third metal layer 143B over the microlenses 140B, and a planarization layer 145 over the third metal layer 143B. The third metal layer 143B may serve a number of different purposes in the biosensor 1300. For example, the third metal layer 143B may help to block incident light from entering the color filter material 127B. In addition, because the third metal layer 143B is curved, any light emitted from a biological or chemical sample may be passed through the microlenses 140B, reflected off of the third metal layer 143B, and directed back toward the color filter material 127B and thus, the light receiving surface of the photodiode 117. In other words, the amount of emitted light that may be measured by the photodiode 117 may be maximized.

The planarization layer 145 may form a planar surface over the third metal layer 143B. The microlenses 140B, the third metal layer 143B, and the planarization layer 145 may have third openings 155A-C formed therein that may overlap with the second openings 150A-C in some embodiments. For example, the third openings 155A-C may have the same width as the second openings 150A-C. However, it is contemplated that in some embodiments, the third openings 155A-C may have a different width than the second openings 150A-C. Together, the second openings 150A-C and the third openings 155A-C may function as spots or wells configured to receive biological or chemical samples, as described further herein. Because the third openings 155A-C of FIG. 13 are deeper than the second openings 150A-C of FIG. 9, excitation light may generally be directed from a source positioned directly above the third openings 155A-C in biosensor 1300. Biosensor 900 may be able to tolerate more angular misalignment of excitation light because second openings 150A-C are not as deep as third openings 155A-C.

Nucleic Acid Sequencing Applications

As described above with respect to FIGS. 2, 8A, 9 and 13, biological or chemical samples may be placed on each of the described biosensors above color filter material 127B and the photodiodes 117. The biological or chemical sample may include any of a number of components. For example, the sample may contain nucleic acid macromolecules (e.g., DNA, RNA, etc.), proteins, and the like. The sample may be analyzed to determine a gene sequence, DNA-DNA hybridization, single nucleotide polymorphisms, protein interactions, peptide interactions, antigen-antibody interactions, glucose monitoring, cholesterol monitoring, and the like.

As discussed above, in some embodiments the biomolecule is a nucleic acid, such as DNA. Without limitation, the DNA biomolecule may be a DNA nanoball (single stranded concatemer) hybridized to labeled probes (e.g., in DNB sequencing by ligation or cPAL methods) or to complementary growing strands (e.g., in DNB sequencing by synthesis methods) or both; or to a single DNA molecule (e.g., in single molecule sequencing); or to a clonal population of DNA molecules, such as is created in bridge PCR based sequencing. Thus, reference to "a biomolecule", "a DNA macromolecule" or "a nucleic acid macromolecule" may encompass more than one molecule (e.g., a DNB associated with multiple growing complementary strands or a DNA cluster comprising clonal population of hundreds or thousands of DNA molecules). See, e.g., U.S. Pat. No. 8,133,719; U.S. Pat. App. Pub. No. 2013/0116153, U.S. Pat. App. Pub. No. 2016/0237488; U.S. Pat. App. Pub. No. 2012/0224050; U.S. Pat. Nos. 8,133,719; 7,910,354; 9,222,132; 6,210,891; 6,828,100, 6,833,246; and 6,911,345, herein incorporated by reference in their entireties.

In some embodiments, the nucleic acid macromolecules may be amplicons of genomic DNA fragments or a cDNA library. As used herein, an "amplicon" may be the product of amplification of a nucleic acid molecule, typically a fragment of genomic DNA or a cDNA library. Methods of amplification include, but are not limited to, rolling circle amplification, as described, for example, in U.S. Pat. No. 8,445,194 (herein incorporated by reference in its entirety), or bridge polymerase chain reaction (PCR), as described, for example, in U.S. Pat. No. 7,972,820 (herein incorporated by reference in its entirety). The amplification may be performed before the nucleic acid is contacted with the biosensor, or in situ, as described, for example, in U.S. Pat. No. 7,910,354, herein incorporated by reference in its entirety.

In some embodiments, color filter material 127B may be sized and functionalized to receive (in spots or wells above color filter material 127B) biological or chemical samples and to absorb light emitted from the biological or chemical sample in some examples. For example, if color filter material 127B is red and the emitted light from the biological or chemical sample is green, color filter material 127B may absorb the green emitted light. In some embodiments, color filter material 127B may be sized and functionalized to receive (in spots or wells above color filter material 127B) biological or chemical samples and to pass light emitted from the biological or chemical sample through the color filter material 127B and onto the light receiving surface of the photodiode 117. For example, if color filter material 127B is blue and the emitted light from the biological or chemical sample is blue, color filter material 127B may pass the blue emitted light through to the light receiving surface of the corresponding photodiode 117. In other words, in some embodiments, emitted light may be absorbed by color filter material 127B. In some embodiments, emitted light may be transmitted through the color filter material 127B and onto the photodiode 117.

For example, a biological sample, such as a DNA macromolecule, oligonucleotide, or nucleotide, associated with a fluorescent or chemiluminescent dye, may be placed above a photodiode 117. In the case of fluorescence, the dye may be illuminated by excitation light from an excitation light source. The excitation light may correspond to any suitable type or intensity of light, including, for example, visible light, infrared (IR), ultraviolet (UV), and the like. The excitation light may also come from any suitable source, such as light emitting diodes (LEDs), lamps, lasers, combinations thereof, and the like. When the dye is illuminated with excitation light at a certain wavelength, the biological sample may absorb the light, then emit light of a different wavelength. For example, the biological sample may absorb excitation light having a 450 nm wavelength, but emit light with a 550 nm wavelength. In other words, fluorescent light of a characteristic wavelength may be emitted when the dye is illuminated by light of a characteristic different wavelength (i.e., the excitation light source). Because excitation light is used to measure fluorescence, however, it must be filtered out in order to take accurate measurements at the photodiode 117.

In the case of chemiluminescence, no excitation light source is needed for the photodiode 117 to detect emitted light. Instead, the biological sample may emit light due to a chemical or enzymatic reaction that may occur between the biological sample and the chemiluminescent dye (or other solution), causing light to be emitted due to breaking or forming chemical bonds.

For both fluorescence and chemiluminescence, the photodiode 117 may detect the intensity of the emitted light and transform it into an electronic signal based on the intensity of the light that may be provided to an external device via metal wiring 113. The external device may correlate the electronic signal to a particular wavelength and brightness, based on the electronic signal and the color of the color filter material 127B used above that particular photodiode 117.

To achieve high density and assist in alignment between the nucleic acid macromolecules and the photodiodes 117 of the biosensor, the surface of the biosensor may be constructed such that there are active spots or wells (e.g., openings 150A-C, openings 155A-C, etc.) that are sized and chemically functionalized to receive a nucleic acid macromolecule, surrounded by areas of the surface to which the nucleic acid macromolecules may not bind. The nucleic acid macromolecules may be secured to the active surface aligned with the photodiode 117 using any suitable surface chemistry. This may include non-covalent interaction (for example, to an area bearing positive charge) or interaction with a capture probe or oligonucleotide attached to the surface, bearing a sequence that is complementary to a sequence contained in the nucleic acid macromolecule. See, for example, U.S. Pat. No. 8,445,194, which is herein incorporated by reference in its entirety.

In some embodiments, the active spot or well on the surface of the biosensor and the nucleic acid macromolecule may be mutually configured such that each spot binds only one nucleic acid macromolecule. This may be achieved, for example, by contacting the surface with amplicons that correspond in size to the active spot (e.g., an amplicon having a diameter that is effectively as large or larger than the diameter of the active spot). See U.S. Pat. No. 8,445,194, herein incorporated by reference in its entirety. Alternatively, the active spot can be chemically adapted to bind a single DNA fragment, which may then be amplified to fill a larger region at and around the original binding site.

Some embodiments of the invention may be used to determine different labels corresponding to different wavelengths of light. The labels may be, for example, fluorescent, chemiluminescent or bioluminescent labels. For example, in gene sequencing (or DNA sequencing), embodiments of the invention may be used to determine the precise order of nucleotide bases within a nucleic acid macromolecule (e.g., a strand of DNA). The nucleotide bases may be labeled with a specific fluorescent label (e.g., adenine (A), guanine (G), cytosine (C), or thymine (T)). Alternatively, one color, two color, or three color sequencing methods, for example, may be used.

With respect to fluorescence, each of the nucleotide bases may be determined in order by successively exciting the nucleic acid macromolecule with excitation light. The nucleic acid macromolecule may absorb the excitation light and transmit an emitted light of a different wavelength onto a biosensor as described herein (e.g., as shown in FIG. 2, 8A, 9 or 13). The biosensor may measure the wavelength of emitted light and intensity received by the photodiode. Each nucleotide, when excited by excitation light of a certain wavelength and/or intensity, may emit a certain wavelength of light and/or intensity into the photodiode (i.e., a "fluorescent label"), allowing identification of the presence of a particular nucleotide base at a particular position in the nucleic acid macromolecule. Once that particular nucleotide base has been determined, it may be removed from the nucleic acid macromolecule, such that the next successive nucleotide base may be determined according to a similar process.

A nucleic acid macromolecule may be labeled with one or more different fluorescent, chemiluminescent, or bioluminescent labels before or after attaching to the biosensor for any purpose. For example, the nucleic acid macromolecule may be hybridized with a labeled oligonucleotide probe or amplification primer. Alternatively, the nucleic acid macromolecule may be hybridized with a non-labeled oligonucleotide, which may then be ligated to a labeled probe, or extended using labeled nucleotide analogs. By way of illustration, the labeling may be done for the purpose of characterizing the nucleic acid macromolecule (for example, the presence of a single nucleotide polymorphism (SNP) associated with a disease), or for nucleic acid sequencing of all or a part of the nucleic acid macromolecule, as described above. DNA sequencing by probe hybridization is described, for example, in U.S. Pat. No. 8,105,771, herein incorporated by reference in its entirety. Sequencing by anchor probe ligation is described, for example, in U.S. Pat. No. 8,592,150, herein incorporated by reference in its entirety. Sequencing by synthesis is described, for example, in U.S. Pat. No. 7,883,869, herein incorporated by reference in its entirety. In general, sequencing by synthesis is a method in which nucleotides are added successively to a free 3' hydroxyl group provided by a sequencing primer hybridized to a template sequence, resulting in synthesis of a nucleic acid chain in the 5' to 3' direction. In one approach, another exemplary type of SBS, pyrosequencing techniques may be employed (Ronaghi et al., 1998, Science 281:363).

In some embodiments, the biosensor shown in FIGS. 2, 8A, 9 and 13 may be coupled to a flow cell (not shown). The nucleic acid macromolecule may be attached to the biosensor by contacting the biosensor with a liquid sample in the flow cell. The flow cell may include one or more flow channels that are in fluid communication with the reaction sites (e.g., openings 150A-C, openings 155A-C, etc.). In one example, the biosensor may be fluidically and electrically coupled to a bioassay system. The bioassay system may deliver reagents to the reaction sites according to a predetermined protocol and perform imaging events. For example, the bioassay system may direct solutions to flow along the reaction sites. The solution may include four types of nucleotides having the same or different fluorescent labels. The bioassay system may then illuminate the reaction sites using an excitation light source. The excitation light may have a predetermined wavelength or wavelengths. The excited fluorescent labels may provide emission signals that may be detected by the photodiodes 117.

A user may prepare for sequencing by contacting a biosensor according to described embodiments (e.g., in FIGS. 2, 8A, 9 and 13) with nucleic acid amplicons, or with a nucleic acid that is subsequently amplified, such that the nucleic acid macromolecule binds and is retained by the active spots or wells, and excess nucleic acid macromolecule may be washed away. The nucleic acid macromolecules may be contacted beforehand or in situ with a labeled reagent. The biosensor may then be operated as described herein to determine light emitted on or around nucleic acid macromolecules on the array. The light may be quantified, or it may be sufficient to determine in a binary fashion which of the nucleic acid macromolecules on the surface have been labeled with labels that emit at a particular wavelength. Different probes or different nucleic acid analogs may be used concurrently that have labels that emit light at different wavelengths, for example, to determine different bases at a particular position in the sequence, or to sequence multiple locations.

EXAMPLE

This example demonstrates that BSI CIS sensors may be used to detect weak signals from surface attached photon emitting molecules. We constructed a biosensor as described in FIG. 9, but without a color filter layer (i.e., lacking elements 120, 123B, 125, and 127B). In addition, surface 133B was rendered hydrophobic, and the bottom surfaces of openings 150A/B/C were rendered hydrophilic (such that DNBs were distributed toward the hydrophilic surfaces and away from the hydrophobic surfaces).

A dilute solution of DNA nanoballs (DNBs) was applied the biosensor array allowing individual DNBs to settle on the spots of the array. For purposes of this experiment all of the DNBs have the same sequence, in contrast to sequencing methods in which essentially all DNBs on an array will have different sequences, and in which the sequence of a DNB are any specific spot/position will not be known prior to sequence determination.

Two primers were hybridized to the DNA templates (see FIG. 15A, top). The "left" primer has a blocked (nonextendible) 3' terminus and is labeled at the 5' terminus with a fluorescent dye. The fluorescent dye was used to establish the position of the DNBs on the array (not shown). The "right" primer acts as an extendible primer for sequencing by synthesis. Sequencing reagents and detection reagents 4 were added (DNA polymerase, streptavidin, biotinylated luciferase 3, ATP and luciferin) along with dATP tagged with biotin via a cleavable linker. In this system the streptavidin 2 associates with the biotin conjugated to the incorporated nucleotide and also associates with biotinylated luciferase, as shown in FIG. 15A. (Biotin 1 symbolized by diamond.) The ATP acts as a substrate for the generation of light by the luciferase-mediated conversion of luciferin to oxyluciferin. The light is received by the photodiodes, generating a signal. The signal is correlated with incorporation of dATP, indicating the present of thymine at the corresponding position of the template sequence. FIG. 15A shows signal from DNBs at numerous spots on the array.

THPP was then used to cleave the cleavable linker, releasing the biotin/streptavidin/luciferase complex, and the array was washed to remove all soluble reagents. FIG. 15B shows that following the wash step signal from the array is absent or significantly reduced.

A second incorporation round was carried out using dTTP-digoxin and DNA polymerase as shown in FIG. 15C. The incorporation of dTTP is detected using a biotinylated anti-digoxin antibody, streptavidin, biotinylated luciferase, ATP and luciferin. The use of biotinylated anti-digoxin antibody amplifies the signal generated by each incorporation event. FIG. 15C is an image showing that chemiluminscent light was generated at numerous spots on the array. This example demonstrates, using two different dNTPs and two different detection systems, that the BSI CIS sensors of the invention may be used to detect weak signals from surface attached photon emitting molecules such as DNBs.

Although the processes described herein are described with respect to a certain number of steps being performed in a certain order, it is contemplated that additional steps may be included that are not explicitly shown and/or described. Further, it is contemplated that fewer steps than those shown and described may be included without departing from the scope of the described embodiments (i.e., one or some of the described steps may be optional). In addition, it is contemplated that the steps described herein may be performed in a different order than that described.

In the foregoing description, aspects of the application are described with reference to specific embodiments thereof, but those skilled in the art will recognize that the invention is not limited thereto. Thus, while illustrative embodiments of the application have been described in detail herein, it is to be understood that the inventive concepts may be otherwise variously embodied and employed, and that the appended claims are intended to be construed to include such variations, except as limited by the prior art. Various features and aspects of the above-described invention may be used individually or jointly. Further, embodiments can be utilized in any number of environments and applications beyond those described herein without departing from the broader spirit and scope of the specification. The specification and drawings are, accordingly, to be regarded as illustrative rather than restrictive. For the purposes of illustration, methods were described in a particular order. It should be appreciated that in alternate embodiments, the methods may be performed in a different order than that described.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

What is claimed is:

1. A biosensor comprising:
   a backside illumination complementary metal-oxide-semiconductor (CMOS) image sensor including:
   an electronic circuit layer; and
   a photo sensing layer over the electronic circuit layer, wherein the photo sensing layer includes:
   a substrate layer, and
   a plurality of photodiodes in contact with the electronic circuit layer, and wherein
   a light receiving surface is defined by a surface of the plurality of photodiodes opposite to the electronic circuit layer;
   a passivation layer on the plurality of photodiodes, wherein the passivation layer is an oxide;
   a regular array of spots formed on the passivation layer above the light receiving surface, wherein the spots of the regular array have uniform dimensions and are organized in a pattern in columns and rows, wherein each spot is a discrete positively charged area sized and functionalized to receive and retain a nucleic acid macromolecule, wherein each spot of the array of spots is separated from other spots by areas that are inert in the sense that they are configured to not receive and retain nucleic acid macromolecules, and wherein the biosensor does not comprise a color filter layer configured to filter light by wavelength range using a polymer material;
   wherein each of the plurality of photodiodes is characterized by a first linear dimension and the regular array of spots are each characterized by a second linear dimension, and the second linear dimension is smaller than the first linear dimension.

2. The biosensor of claim 1, wherein the inert areas are characterized by hydrophobic surfaces.

3. The biosensor of claim 2, wherein each spot is sized and functionalized to contain a DNA nanoball (DNB).

* * * * *